US010842897B2

(12) United States Patent
Schwartz et al.

(10) Patent No.: US 10,842,897 B2
(45) Date of Patent: Nov. 24, 2020

(54) DISINFECTING ARTICLES WITH OZONE

(71) Applicant: Éclair Medical Systems, Inc., Portland, OR (US)

(72) Inventors: Peter V. Schwartz, Livermore, CA (US); Scott Anthony Garvey, Portland, OR (US); Jonathan W. Carmichael, Portland, OR (US); Eric Randall Meier, Portland, OR (US); Judith Apsay Guzman-Cottrill, Portland, OR (US)

(73) Assignee: ÉCLAIR MEDICAL SYSTEMS, INC., Portland, OR (US)

( * ) Notice: Subject to any disclaimer, the term of this patent is extended or adjusted under 35 U.S.C. 154(b) by 238 days.

(21) Appl. No.: 15/877,036

(22) Filed: Jan. 22, 2018

(65) Prior Publication Data
US 2018/0207307 A1    Jul. 26, 2018

Related U.S. Application Data

(60) Provisional application No. 62/448,751, filed on Jan. 20, 2017, provisional application No. 62/448,767,
(Continued)

(51) Int. Cl.
*A61L 2/20* (2006.01)
*A61L 2/24* (2006.01)
(Continued)

(52) U.S. Cl.
CPC ............... *A61L 2/202* (2013.01); *A61L 2/10* (2013.01); *A61L 2/24* (2013.01); *A61L 9/20* (2013.01);
(Continued)

(58) Field of Classification Search
CPC ... A61L 2/202; A61L 2/24; A61L 2/10; A61L 2202/11; A61L 2202/24; A61L 2202/13;
(Continued)

(56) References Cited

U.S. PATENT DOCUMENTS 4,335,075 A * 6/1982 Kackos ................... F16J 15/46
220/232
4,909,996 A    3/1990 Uys
(Continued)

FOREIGN PATENT DOCUMENTS

EP           1175230        1/2002
WO    WO-2015117233 A1 *  8/2015  ......... G01N 33/0039

OTHER PUBLICATIONS

"Ozone And How It Can Affect Your Health" Disabled World, Disabled World, Jun. 7, 2013, www.disabled-word.com/medical/ozone.php.
(Continued)

*Primary Examiner* — Regina M Yoo
(74) *Attorney, Agent, or Firm* — David R. Stevens; Stevens Law Group

(57) ABSTRACT

The present invention extends to methods, apparatus, and systems for disinfecting articles with ozone. Aspects of the invention use increased concentrations ozone in sealed, confined volumes, such as, for example, carts, lockers, cabinets, etc. to disinfect or sterilize medical articles. A medical article is placed in a confined volume. The confined volume is sealed so that the atmosphere inside the sealed, confined volume is isolated from the external atmosphere. The concentration of ozone in the sealed, confined volume is rapidly increased to a threshold concentration. At the threshold ozone concentration, the medical article can be disinfection or sterilized in a reduce amount of time. When disinfection or sterilization is complete, the concentration of ozone in the sealed, confined volume is rapidly reduced to
(Continued)

a safe level. The sealed, confined volume is unsealed. The disinfected or sterilized medical article can be removed from the confined volume.

20 Claims, 16 Drawing Sheets

Related U.S. Application Data filed on Jan. 20, 2017, provisional application No. 62/448,779, filed on Jan. 20, 2017.

(51) Int. Cl.
*A61L 2/10* (2006.01)
*A61L 9/20* (2006.01)
*G01N 21/33* (2006.01)

(52) U.S. Cl.
CPC ...... *A61L 2202/11* (2013.01); *A61L 2202/121* (2013.01); *A61L 2202/122* (2013.01); *A61L 2202/13* (2013.01); *A61L 2202/14* (2013.01); *A61L 2202/24* (2013.01); *G01N 21/33* (2013.01)

(58) Field of Classification Search
CPC ........... A61L 2202/122; A61L 2202/14; A61L 2202/121; A61L 9/20; G01N 21/33
See application file for complete search history.

(56) References Cited

U.S. PATENT DOCUMENTS

| | | | |
|---|---|---|---|
| 5,120,512 A * | 6/1992 | Masuda | A61L 2/202 422/198 |
| 6,060,020 A * | 5/2000 | Piuk | A61L 2/202 422/33 |
| 6,360,324 B2 | 3/2002 | Van Blarkom | |
| 7,475,405 B2 | 1/2009 | Manganaris | |
| 7,658,891 B1 * | 2/2010 | Barnes | A61L 9/015 128/205.28 |
| 7,774,363 B2 | 8/2010 | Lim | |
| 8,250,630 B2 | 8/2012 | Mendonca | |
| 8,356,027 B2 | 1/2013 | Jaecksch | |
| 8,465,704 B2 | 6/2013 | Watson | |
| 8,595,834 B2 | 11/2013 | Xie | |
| 8,769,684 B2 | 7/2014 | Stolfo | |
| 8,826,370 B2 | 9/2014 | Boukobza | |
| 8,930,410 B2 | 1/2015 | Alton | |
| 8,983,985 B2 | 3/2015 | Chen | |
| 9,171,182 B2 | 10/2015 | Shukla | |
| 9,400,879 B2 | 7/2016 | Tredoux | |
| 9,418,384 B1 | 8/2016 | Middleman | |
| 9,536,072 B2 | 1/2017 | Guedalia | |
| 9,621,680 B2 | 4/2017 | D'Costa | |
| 9,633,227 B2 | 4/2017 | Tang | |
| 9,715,528 B2 | 7/2017 | Ho | |
| 9,762,603 B2 | 9/2017 | Grondin et al. | |
| 9,946,780 B2 | 4/2018 | Gerweck | |
| 10,391,527 B2 * | 8/2019 | Boin | C01B 13/11 |
| 2005/0012281 A1 * | 1/2005 | Ludwig | F16J 15/46 277/646 |
| 2005/0226795 A1 * | 10/2005 | Drummond | A61L 2/26 422/293 |
| 2014/0193294 A1 * | 7/2014 | Kain | A61L 2/24 422/3 |
| 2015/0004061 A1 * | 1/2015 | Kain | A61L 2/24 422/116 |
| 2017/0238568 A1 * | 8/2017 | Elrod | G01N 33/0004 |
| 2017/0246333 A1 * | 8/2017 | Carbone | A61L 2/202 |

OTHER PUBLICATIONS

Atkinson et al. "Concepts and Types of Ventilation", Natural Ventilation for Infection Control Health-care settings, U.S. National Library of Medicine, Jan. 1, 1970 www.ncbi.nlm.nih.gov/books/NBK143277/.

* cited by examiner

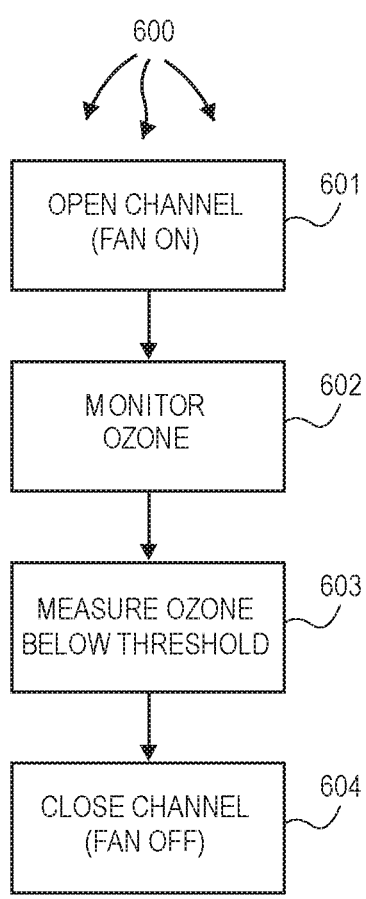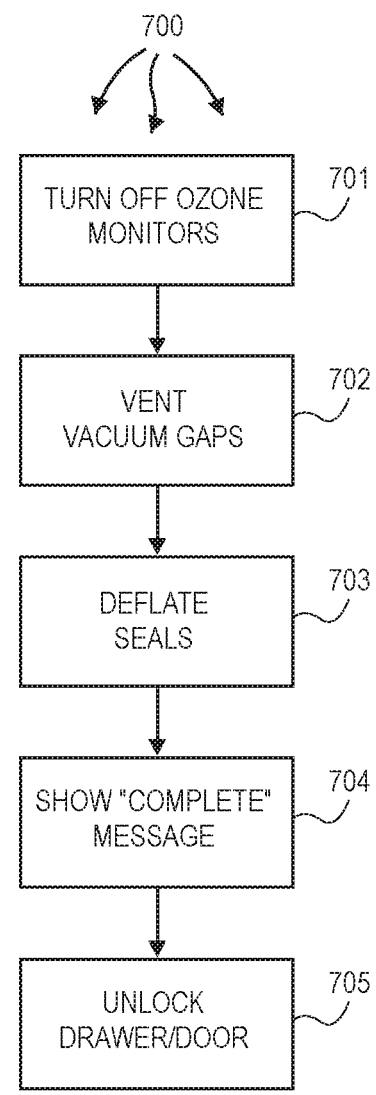
FIG. 6
FIG. 7

DISINFECTING ARTICLES WITH OZONE

CROSS-REFERENCE TO RELATED APPLICATIONS

This application claims the benefit of U.S. Provisional Application No. 62/448,751, filed Jan. 20, 2017, U.S. Provisional Application No. 62/448,767, filed Jan. 20, 2017, and U.S. Provisional Application No. 62/448,779, filed Jan. 20, 2017. These applications are incorporated herein by reference for all purposes.

BACKGROUND

1. Field of the Invention

This invention relates generally to disinfecting items, and, more particularly, to disinfecting and sterilizing medical related equipment and supplies using ozone.

2. Related Art

A variety of mechanisms are used in medical environments to mitigate patient exposure to pathogens. For example, equipment and supplies used in hospital and surgical environments can be disinfected and possibly sterilized before use. Disinfection and sterilization prevent the spread of pathogens via respiratory droplets and via direct patient contact with equipment and supplies. Equipment and supplies can be sterilized prior to and/or after use to mitigate the spread of pathogens.

BRIEF DESCRIPTION OF THE DRAWINGS

The specific features, aspects and advantages of the present invention will become better understood with regard to the following description and accompanying drawings where:

FIG. 6 illustrates a flow chart of an example method for implementing a reduction cycle.

FIG. 7 illustrates a flow chart of an example method for implementing an open cycle.

DETAILED DESCRIPTION

Figure 1:
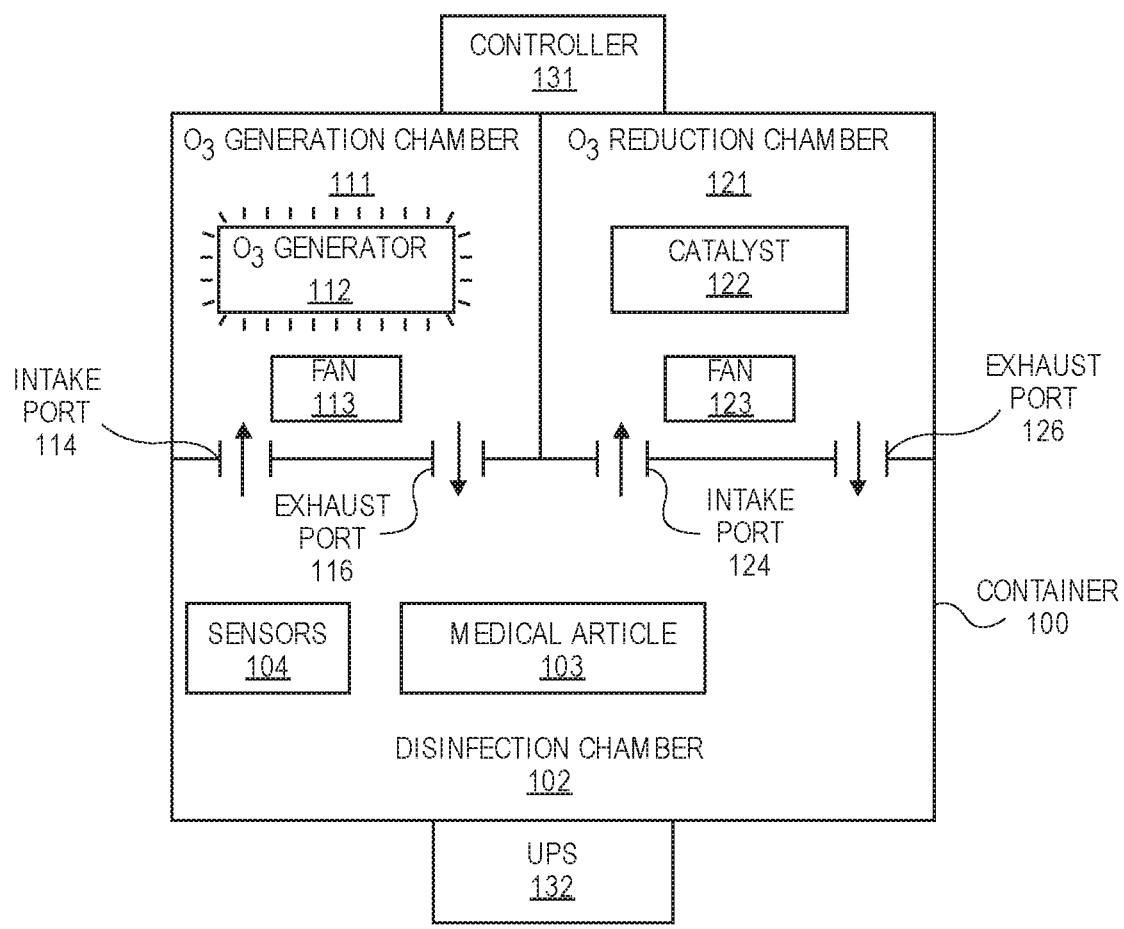
FIG. 1 illustrates an example diagram of a container for disinfecting a medical article.

The present invention extends to methods, apparatus, and systems for disinfecting articles with ozone.

In general, disinfecting and/or sanitizing medical articles in a healthcare facility or other healthcare environment can reduce patient exposure to pathogens. As such, various disinfecting and sterilization techniques have been developed to disinfect and/or sterilize medical articles.

An authoritative government entity can classify medical articles (e.g., devices, tools, equipment, clothing, linen, packaging, etc.) according to the degree of risk of infection associated with use of the medical article. For example, in the United States, the Food and Drug Administration ("FDA") can classify medical articles as critical, semi-critical, or non-critical. Critical medical articles (e.g., sutures, staples, surgical instruments, etc.) come in contact with blood or normally sterile tissue. Semi-critical medical articles (e.g., endoscopes) come in contact with mucus membranes. Non-critical medical articles (e.g., stethoscopes) come in contact with unbroken skin.

Some sterilization techniques use heating, chemical disinfection, exposure to ultra-violet radiation, and nuclear irradiation. However, limitations prevent these sterilization techniques being effective for many applications. For example, high temperatures of autoclaves may damage plastic or rubber components. Special regulations regarding storage and handling of potentially hazardous chemicals limits their ease of use. UV radiation requires line-of sight exposure for maximum effectiveness and limits its use on objects, such as, clothing that has internal and external facing surfaces. The use of nuclear radiation is can be effective but can only be performed in special installations.

Some techniques have used ozone in a limited capacity to expose smaller medical articles, such as, for example, staples, catgut, surgical instruments, and other smaller critical devices, to a sterilization environment. Ozone interferes with the metabolism of bacterium-cells and can break through cell membrane leading to the destruction of viruses, bacteria, and spores. However, these sterilization techniques rely on long exposure times at low concentration. As such, these sterilization techniques are less practical for some types of medical articles, including bulkier and/or reusable semi-critical, non-critical, or non-categorized medical articles. The practicality of these sterilization techniques reduces in direct proportion to turnaround time for reusing a medical article (to possible impracticality). That is, these sterilization techniques become less practical the shorter the turnaround time is for reuse a medical article.

Aspects of the invention use increased concentrations ozone in sealed, self-contained environments, such as, for example, carts, lockers, cabinets, tumblers, etc. to disinfect or sterilize medical articles. The carts, lockers, cabinets, tumblers, etc. can be used to disinfect and sterilize hospital supplies and wearable hospital accessories, possibly contaminated with disease-spreading pathogens including bacteria, viruses, and mold. Disinfection and/or sterilization is achieved by using highly concentrated ozone in isolated, confined, volumes to destroy contaminants that contribute to Hospital Associated Infections (HAI).

For example, a medical article is placed in a self-contained environment. The self-contained environment is sealed so that the atmosphere inside the sealed, self-contained environment is isolated from the external atmosphere. The concentration of ozone in the sealed, self-contained environment is rapidly increased to a threshold concentration. At the threshold ozone concentration, the medical article can be disinfection or sterilized in a reduced amount of time. When disinfection or sterilization is complete, the concentration of ozone in the sealed, self-contained environment is rapidly reduced to a safe level. The sealed, self-contained environment is unsealed. The disinfected or sterilized medical article can be removed from the self-contained environment.

Accordingly, aspects of the invention reliably, safely, and non-destructively expose medical articles to higher concentrations of zone to disinfect and/or sterilize the medical articles in reduced periods of time. A self-contained environment can include an ozone generator. The self-contained environment is configured so that atmosphere inside passes (or recirculates) through the ozone generator multiple times within the natural half-life of ozone. Thus, higher concentrations of ozone can be achieved inside the self-contained environment.

As the concentration of ozone in the self-contained environment increases, the time to disinfect and/or sterilize medical articles in the self-contained environment decreases. Subsequent to disinfection and/or sterilization, the ozone concentration in the self-contained environment is relatively quickly (e.g., rapidly) reduced. Disinfected and/or sterilized medical articles can then be safely and efficiently handled. In one aspect, ozone concentration is reduced by venting the atmosphere out of the self-contained environment into a suitable catalyst (e.g., Manganese Dioxide ("$MnO_2$")) to convert ozone ("$O_3$") to oxygen ("$O_2$"). As such, medical articles can be disinfected and/or sanitized in a relatively short amount of time without contaminating or polluting a surrounding environment.

Virtual any type of medical article that contacts with intact skin and that may be exposed to organic soil during patient care (e.g. bodily fluids, blood, bacteria, viruses, sweat) can be disinfected and/or sanitized in a reduced time period. Medical articles include medical vesture, such as, surgical protective equipment worn in surgery, medical supplies used in isolation environments, x-ray aprons (and other protective lead wearables), eye protection, footwear, hospital linens, packaging, etc.

In this description and the following claims, "ozone" (or "trioxygen") is defined as an inorganic molecule with the chemical formula $O_3$. The terms ozone and $O_3$ are used interchangeably throughout the description and claims. Ozone interferes with the metabolism of bacterium-cells and can break through cell membrane leading to the destruction of viruses, bacteria, and spores. Exposing medical articles to higher concentrations of ozone reduces the time to disinfect or sterilize the medical articles.

In this description and the following claims, "disinfection" is defined as a decontamination process of eliminating or reducing harmful microorganisms from inanimate objects and surfaces.

In this description and the following claims, "sterilization" is defined as a decontamination process of killing all microorganisms and their spores from inanimate objects and surfaces. As such, sterilization is contained within the definition of disinfection and can be considered a more rigorous disinfection process. Throughout the description, the terms "disinfection", "disinfected", and "disinfecting" are defined to include the corresponding terms of "sterilization", "sterilized" and "sterilizing" respectively. Thus, when any of the terms "disinfection", "disinfected", and "disinfecting" are used, the corresponding term "sterilization", "sterilized" and "sterilizing" respectively may also be applicable. For clarity, terms stemming from "disinfect" may sometimes be used without express reference to the corresponding term stemming from "sterile," even when those terms are interchangeable.

FIG. 1 illustrates an example block diagram of a container 100 for disinfecting a medical article. As depicted, container 100 includes disinfection chamber 102, sensors 104, ozone generation chamber 111, ozone reduction chamber 121, controller 131, and uninterruptable power source (UPS) 132.

Ozone generation chamber 111 includes ozone generator 112, fan 113, intake port 114, and exhaust port 116. Fan 113 pulls atmosphere from disinfection chamber 102 through intake port 114 into ozone generation chamber 111. Within ozone generation chamber 111, the concentration of ozone in the atmosphere is increased. Atmosphere having an increased concentration of ozone is expelled through exhaust port 116 into disinfection chamber 102. Fan 113 can cause atmosphere inside disinfection chamber 102 to pass through ozone generation chamber 111 multiple times within the natural half-life of ozone. Thus, disinfection chamber 102 can achieve high concentrations of ozone in a reduced period of time.

Catalyst 122 is configured to accelerate the conversion of ozone back into oxygen ($O_2$) to relatively quickly reduce the concentration of ozone in disinfection chamber 102 to a safe level. Catalyst 122 can be Manganese Dioxide ($MnO_2$) (or another ozone compatible material). Fan 123 pulls atmosphere from disinfection chamber 102 through intake port 124 into ozone reduction chamber 121. Within ozone reduction chamber 121, ozone passes through catalyst 122 and is converted to into oxygen ($O_2$). The oxygen ($O_2$) is expelled out of exhaust port 126 into disinfection chamber 102. The amount of catalyst 122 and the velocity ozone travels through catalyst 122 determines how quickly ozone is converted into oxygen ($O_2$). Ozone can be converted to oxygen ($O_2$) in a (possible significantly) reduced period of time relative to the natural half-life of ozone. Complete conversion of ozone to oxygen ($O_2$) can occur in a single pass or multiple passes.

Controller 131 controls activation and deactivation of components in disinfection chamber 102, ozone generation chamber 111, and ozone reduction chamber 121. To increase concentrations of ozone in disinfection chamber 102, controller 131 can turn on ozone generator 112 and fan 113 and open intake port 114 and exhaust port 116 (i.e., controller 131 can activate ozone generation chamber 111). When concentrations of ozone are being increased, controller 131 can also turn off fan 123 and close intake port 124 and exhaust port 126 (i.e., controller 131 deactivate ozone reduction chamber 121). To reduce concentrations of ozone in disinfection chamber 102, controller 131 can turn on fan 123 and open intake port 124 and exhaust port 126 (i.e., controller 131 can activate ozone reduction chamber 121). When concentrations of ozone are being reduced, controller 131 can also turn off ozone generator 112 and fan 113 and close intake port 114 and exhaust port 116 (i.e., controller 131 deactivate ozone generation chamber 111).

Sensors 104 can include one or more ozone sensors inside disinfection chamber 102. In one aspect, sensors 104 includes an ultra-violet (UV) absorption sensor. The UV absorption sensor can be continuously monitored to determine the concentration of ozone in disinfection chamber 102. The UV absorption sensor can include a light emitting diode and a photodiode. The light emitting diode can be configured to emit light of a specified wavelength and the photodiode can be configured to detect light of the specified wavelength. In one aspect, the light emitting diode is configured to emit and the photodiode is configured to detect light having a wavelength between 240 nm-260 nm (i.e., 250 nm, +/−10 nm). In another aspect, the light emitting diode is configured to emit and the photodiode is configured to detect light having a wavelength between 250 nm-260 nm (i.e., 255 nm, +/−5 nm).

Ultra-violet light from the emitter is absorbed by any ozone in the atmosphere. Thus, the amount of light detected by the photodiode can vary based on the amount of ozone in the disinfection chamber 102. The UV absorption sensor can be used to determine when ozone is present and at what level. As such, the UV absorption sensor can also be used to determine a disinfection or sterilization end point and to determine when it is safe to open container 100.

Container 100 can be connected to mains power. UPS 132 can provide emergency power to the components of container 101 when mains power fails.

Figure 2:
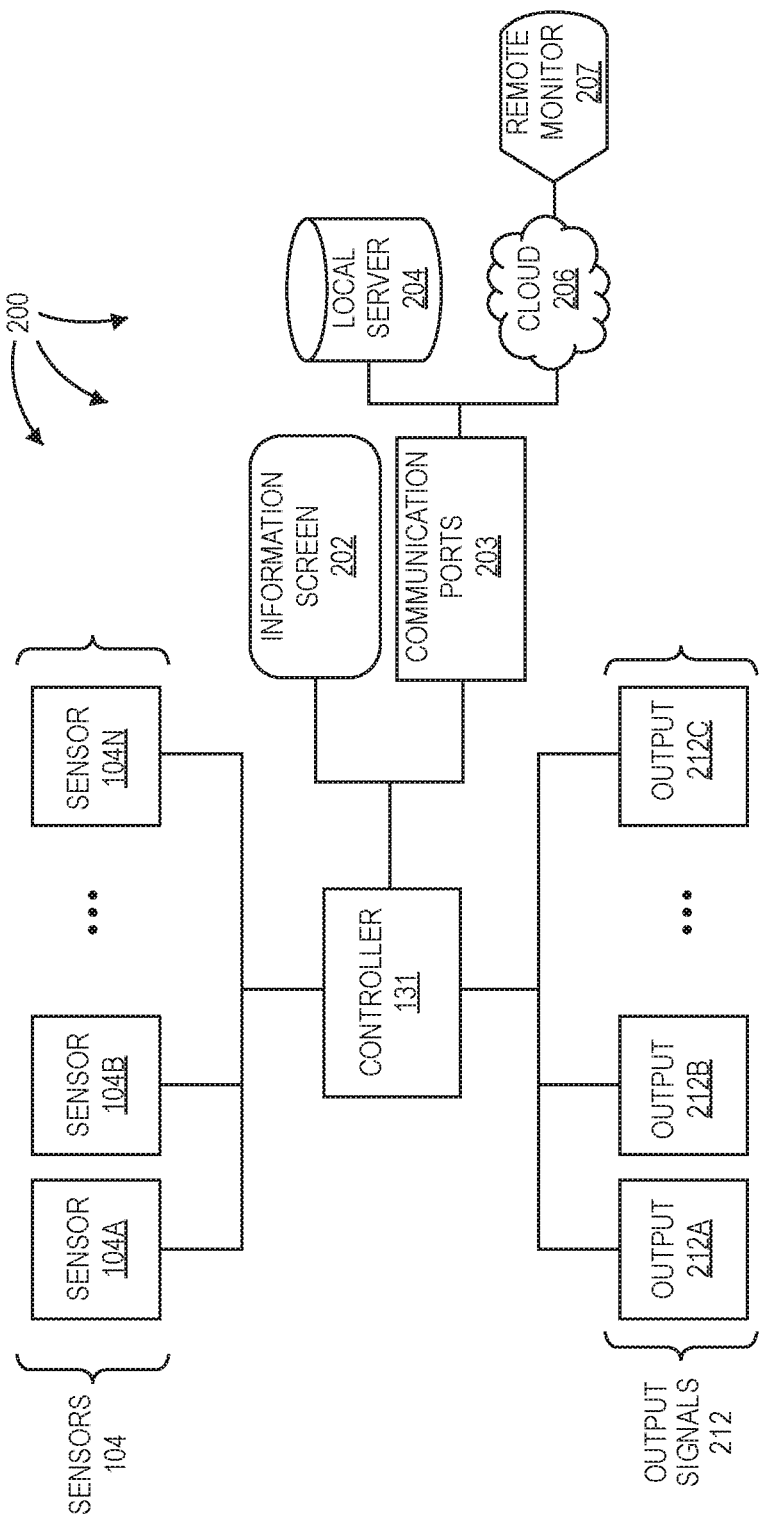
FIG. 2 illustrates an example computer architecture for controlling the container of FIG. 1.

Turning to FIG. 2, FIG. 2 illustrates an example computer architecture 200 for controlling container 100. Computer architecture 200 includes sensors 104, controller 131, information screen 202, communication ports 203, local server 204, cloud 206, and remote monitor service 207.

Sensors 104 includes sensors 104A, 104B through 104N, etc. Controller 131 receives inputs from sensors 104A, 104B through 104N, etc. monitoring contents and/or components of container 100. Sensors 104A, 104B through 104N, etc. can include sensors both internal and external to container 100. As such, inputs received from sensors 104A, 104B through 104N, etc. can be used to monitor environments internal and/or external to container 100. Sensors 104A, 104B through 104N, etc. can include, but are not limited to, voice recognition sensors, light activation sensors, motion sensors, foot activation sensors, badge reading sensors, $O_3$ sensors, Ultra-violet $O_3$ sensors, visible light intensity detector, pressure sensors, fan sensors, flow sensors, atmospheric sensors, loss-of-power sensors, door/drawer lock sensors, door/drawer position sensors, etc.

Controller 131 can use inputs received from sensors 104 to determine the state of disinfection chamber 102 and determine actions to facilitate safe operation of container 100. Disinfection chamber states can include: "in operation", "idle", "disinfected", "sterilized", etc. Controller 131 can control a set of output signals 212 to facilitate safe operation of the disinfection chamber 102. The set of output signals 212 can include different output signals 212A, 212B through 212N used to control devices including, but not limited to, switches, relays, voltage sources, etc. (e.g., that in turn control Ozone generator 112, fans 113 and 123, intake ports 114 and 124, exhaust ports 116 and 126, sensors 104A, 104B through 104N, etc.).

Controller 131 can also send messages to information screen 202 (e.g., located locally at container 100) indicating the state of disinfection chamber 102 (e.g. "in operation", "idle", "disinfected", "sterilized", etc.). In one aspect, information screen 202 also includes a user interface for entering commands to operate the components of container 100.

Controller 131 can also communicate with external devices, for example, using wired and/or wireless communication protocols, through communication ports 203. In one aspect, controller 131 is connected to local server 204. Controller 131 and local server 204 can exchange information via communication ports 203. Information exchanged with server 204 can include the status of disinfection chamber 102 and commands to operate the components of container 100. In another aspect, controller 101 is connected to cloud 206 running remote monitor service 207 (e.g., a cloud based service). Controller 131 can send information to remote monitor service 207, including the status of disinfection chamber 102.

Controller 131 can also use input from sensors 104 to determine operational performance of components at container 100 and to track disinfection of medical articles (e.g., medical article 103) in disinfection chamber 102. Controller 131 can send operational performance information and tracked medial article information to any of information screen 202, local server 204, and remote monitor service 207.

Medical Article Disinfection

Generally, medical article 103 can be placed in disinfection chamber 102 and a drawer, door, etc. can be closed to seal disinfection chamber 102 from the external environment. Controller 131 can activate ozone generation chamber 111. Ozone generation chamber 111 can remain active until disinfection chamber 102 achieves a desired concentration of ozone.

The desired concentration of ozone can be maintained for a specified period of time to disinfect (or fully sterilize) medical article 103. In one aspect, medical article 103 is a semi-critical device or a non-critical device. The desired concentration of ozone can be sufficiently high so that the specified period of time for disinfection is relatively short. For example, exposed surfaces of medical article 103 can be disinfected to achieve a better than 4 log reduction (i.e., 99.99% kill) of contaminants in under 20 minutes.

After the specified time period, controller 131 can deactivate ozone generation chamber 111 and activate ozone reduction chamber 121. Ozone reduction chamber 121 can remain active until ozone concentrations fall below a specified threshold (e.g., below 50 parts-per-billion-atomic (ppba)). Controller 131 then deactivates ozone reduction chamber 121 and (disinfected) medical article 103 can be removed from disinfection chamber 102 for use.

Figures 3, 4:
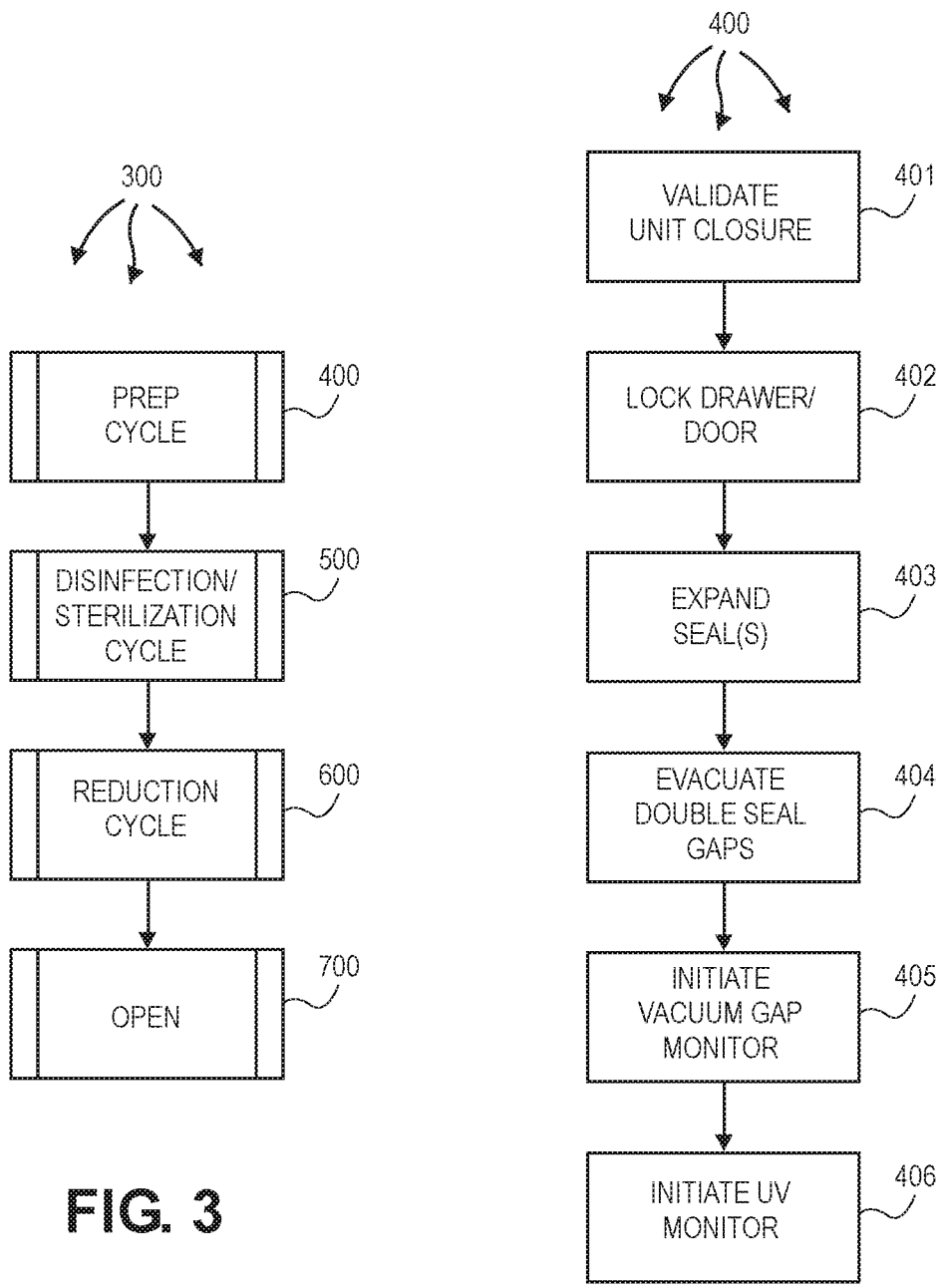
FIG. 3 illustrates a flow chart of an example method for disinfecting a medical article.
FIG. 4 illustrates a flow chart of an example method for implementing a preparation cycle.

More specifically, several different cycles may be implemented to disinfect (or fully sterilize) a medial article. FIG. 3 illustrates a flow chart of an example method 300 for disinfecting a medical article. Method 300 includes a preparation cycle 400, a disinfection/sterilization cycle 500, a reduction cycle 600, and an open cycle 700.

FIG. 4 illustrates a flow chart of an example method for implementing preparation cycle 400. Preparation cycle 400 will be described with respect to the components of container 100 and computer architecture 200. Preparation cycle 400 can be performed upon initiation of a disinfection/sterilization protocol.

To disinfect medical article 103, medical article 103 can be placed inside disinfection chamber 102 and a drawer/door (not shown) of container 100 closed. Preparation cycle 400 includes validating unit closure (401). For example, based on inputs from one or more of sensors 104, controller 131 can validate that the drawer/door at container 100 is closed. Preparation cycle 400 includes locking a drawer/door (402). For example, controller 131 can send one or more of output signals 212 to lock the drawer/door of container 100. Controller 131 can also send one or more of output signals 212 to close intake ports 114 and 124 and close exhaust ports 116 and 126. Controller 131 can also activate an "in operation" light indicator on container 100 and/or indicate that container 100 is "in operation" at information screen 202.

A purge of (e.g., hospital grade) Oxygen ($O_2$) or an oxygen concentrator can be used to increase the Oxygen ($O_2$) concentration in disinfection chamber 102. The length of a purge can be determined from the flow rate of the Oxygen ($O_2$) introduced into disinfection chamber 102 and scaled to accommodate the internal volume of disinfection chamber 102.

Preparation cycle 400 includes expanding seal(s) (403). The drawer/door of container can include a double chamber seal (not shown) with a gap separating the individual seals. Each individual seal can be expanded to seal disinfection chamber 102 from the external environment. After Oxygen ($O_2$) concentration increase, controller 131 can send one or more of output signals 212 to sealing components (now shown) of container 100. The output signals 212 can instruct the sealing components to expand the individual seals of the double chamber seal of the drawer/door. The output signals 212 can also instruct the sealing components to activate other seals, for example, at vents, access points, intake ports 114 and 124, exhaust ports 116 and 126, etc., when appropriate.

Preparation cycle 400 includes evacuating double seal gaps (404). A vacuum/vent port (not shown) can be included in the gap between the individual seals of the double chamber seal. After seal expansion, controller 131 can send one or more of output signals 212 to vacuum components (now shown) at container 100. The output signals 212 can instruct the vacuum components to evacuate the atmosphere in the gap through the vacuum/vent port. The output signals 212 can also instruct the vacuum components to evacuate the atmosphere in gaps of any other double chamber seals at container 100.

Preparation cycle 400 includes initiating a vacuum gap monitor (405). For example, controller 131 can send one or more of output signals 212 to activate one or more of sensors 104 to monitor gaps between the individual seals of any double chamber seals. As such, atmosphere in any gaps between double chamber seals is evacuated and pressure monitoring of the gap is initiated. A detected change in pressure may indicate a seal leak. Preparation cycle 400 includes initiating ultra-violet monitoring (406). For example, controller 131 can send one or more of output signals 212 to activate one or more UV ozone sensors from among sensors 104. The UV ozone sensor(s) can monitor the atmospheric contents of disinfection chamber 102.

Figure 5:
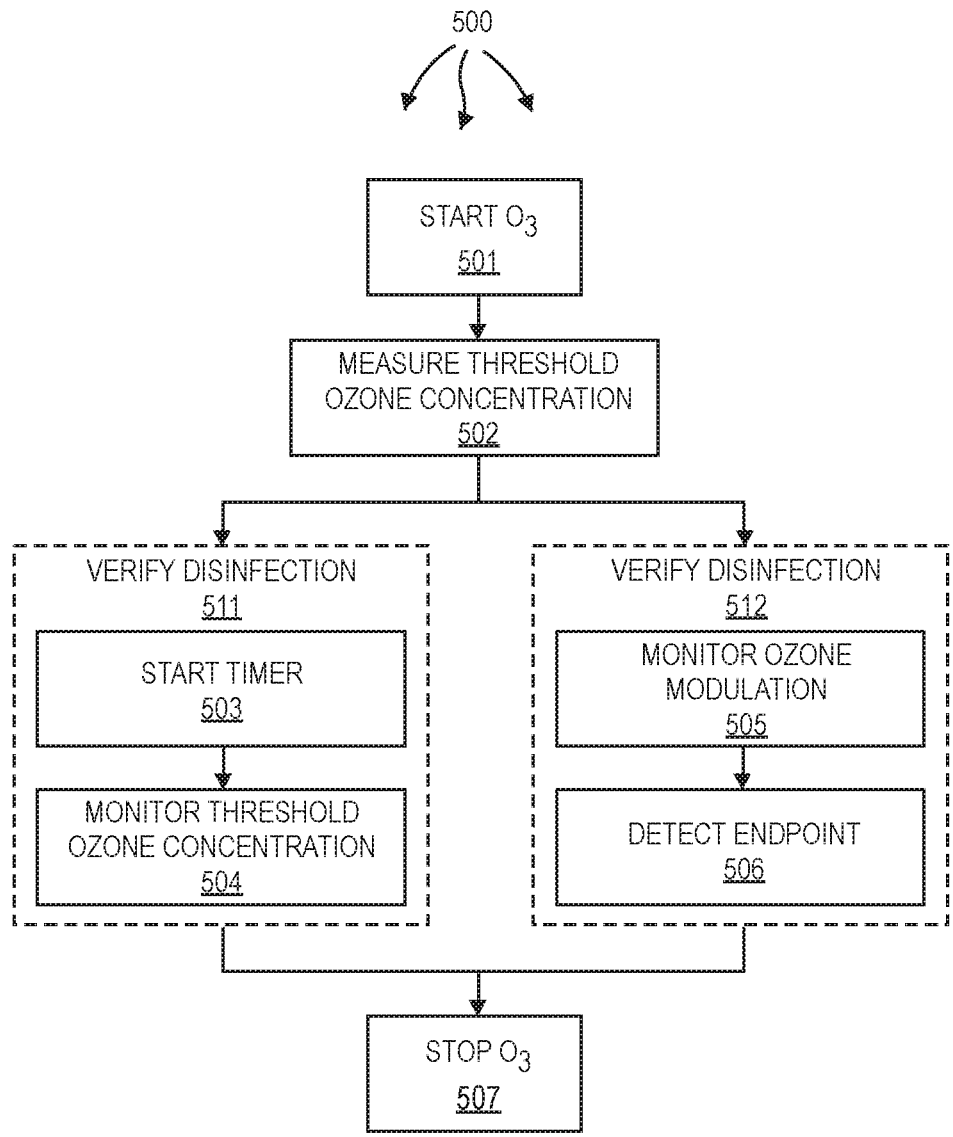
FIG. 5 illustrates a flow chart of an example method for implementing a disinfection/sterilization cycle.

FIG. 5 illustrates a flow chart of an example method for implementing a disinfection/sterilization cycle 500. Disinfection/sterilization cycle 500 can be implemented after disinfection chamber 102 is prepared (e.g., after preparation cycle 400 completes). Disinfection/sterilization cycle 500 includes starting ozone (501). For example, controller 131 can activate ozone generation chamber 111, including turning on ozone generator 112 and fan 113 and opening intake port 114 and exhaust port 116. Fan 113 can pull atmosphere from disinfection chamber 102 through intake port 114 into ozone generation chamber 111.

Ozone generator 112 generates ozone, increasing the ozone concentration of atmosphere in ozone generation chamber 111. Atmosphere with increased ozone concentration then exhausts through exhaust port 116 back into disinfection chamber 102. The atmosphere of disinfection chamber 102 can be allowed to pass through ozone generation chamber 111 multiple times. Since disinfection chamber 102 is sealed, ozone concentrations can build to higher levels in a reduce amount of time.

Disinfection/sterilization cycle 500 includes measuring threshold ozone concentration (502). Controller 131 can allow ozone concentrations in disinfection chamber 102 to increase until a threshold ozone concentration is achieved. The UV ozone sensor(s) can detect the threshold ozone concentration in disinfection chamber 102. A threshold ozone concentration can be application dependent and in the range of 50 parts-per-billion-atomic (ppba) to 5% atomic. The UV ozone sensor(s) can indicate to controller 131 when the threshold ozone concentration is achieved. Controller 131 can send one or more of output signals 212 to deactivate ozone generation chamber 111 or to reduce the generation of ozone so that the ozone concentration is maintained (but not necessarily increasing).

Ozone in disinfection chamber 102 can disinfect medical article 103. Since ozone is in gas form it can surround and disinfect all exposed surfaces of medical article 103.

Different mechanisms can be used to verify disinfection. In one aspect, disinfection/sterilization cycle 500 includes disinfection verification mechanism 511. Disinfection verification mechanism 511 can include starting a timer (502) and monitoring the threshold ozone concentration (503). For example, controller 131 can set a timer indicating a prescribed time period to maintain the threshold ozone concentration in disinfection chamber 102.

The UV ozone sensor(s) can continue to monitor the ozone concentration in disinfection chamber 102 and report the ozone concentration to controller 131. Controller 131 can send one or more of output signals 212 to one or more of: ozone generator 112, fan 113, intake port 114, and exhaust port 116 to maintain the threshold ozone concentration until the prescribed time period elapses (and medical article 103 is sufficiently disinfected). Controller 131 can then send one or more of output signals 212 to deactivate ozone generation chamber 111

In another aspect, disinfection/sterilization cycle 500 includes disinfection verification mechanism 512. Disinfection verification mechanism 512 can include monitoring ozone modulation (505) and detecting an endpoint (506). Controller 131 can analyze the natural decay rate of the ozone concentration and compare this to a sterilized chamber to detect an endpoint. Controller 131 can the send one or more of output signals 212 to deactivate ozone generation chamber 111. The UV ozone sensor(s) can continue to monitor the ozone concentration in disinfection chamber 102 and report the ozone concentration to controller 131. In one aspect, the UV ozone sensor(s) utilizes the absorption properties of 240 nm-260 nm (i.e., 250 nm, +/−10 nm) light by ozone. In another aspect, the UV ozone sensor(s) utilizes the absorption properties of 250 nm-260 nm (i.e., 255 mn, +/−5 nm) light by ozone. Several cycles of modulating ozone generator 112 provide temporal characteristics of ozone reduction to oxygen ($O_2$) (and sufficient disinfection of medical article 103).

Disinfection/sterilization cycle 500 includes stopping ozone (507). For example, controller 131 can deactivate ozone generation chamber 111 when medical article 103 is verified disinfected, including turning off ozone generator 112 and fan 113 and closing intake port 114 and exhaust port 116.

FIG. 6 illustrates a flow chart of an example method for implementing a reduction cycle 600. Reduction cycle 600 can transform ozone back into oxygen ($O_2$). The natural reduction of ozone to oxygen ($O_2$) can be at least 20 half-life time units to reach levels the Occupational Safety and Health Administration (OSHA) has deemed safe (<50 ppba). To speed the rate of reduction, reduction cycle 600 can used catalyst 122. Catalyst 122 is configured to destroy high concentrations of ozone. Catalyst 122 can be contained in a reduction vessel (not shown) that has an opening at each end. On one open end (e.g., intake port 124), fan 123 or some other blower is mounted to force the atmosphere from disinfection chamber 102 through the reduction vessel and out the other open end (e.g., exhaust port 126). The reduction vessel is isolated from disinfection chamber 102 by vent flaps that seal off each end of the reduction vessel when not in use.

Reduction cycle 600 includes opening the channel (fan on) (601). For example, controller 131 can the send one or more of output signals 212 to open intake port 124, open exhaust port 126, and turn on fan 123. Atmosphere in disinfection chamber 102 is diverted through ozone reduction chamber 121 where ozone is converted back into oxygen ($O_2$). In one aspect, ozone is forced through a matrix of Manganese Dioxide ("$MnO_2$")) where the reduction of ozone to oxygen ($O_2$) is catalyzed providing an increased rate of conversion.

Reduction cycle 600 includes monitoring ozone concentration (602). For example, the UV ozone sensor(s) can monitor the ozone concentration in disinfection chamber 102 as reduction is occurring. Reduction cycle 600 includes measuring ozone below a threshold (603). For example, the UV ozone sensor(s) can measure ozone concentration in disinfection chamber 102 to be below a threshold (e.g., a safe level of <50 ppba). The atmosphere of disinfection chamber 102 can be recycled through catalyst 122 (e.g., the matrix of manganese dioxide ("$MnO_2$")) A sufficient number of times to reduce ozone concentration below the threshold and/or to safe levels.

Reduction cycle 600 includes closing the channel (fan off) (604). For example, UV ozone sensor(s) can indicate to controller 131 when ozone concentration is below the threshold and/or at a safe level. Controller 131 can send one or more of output signals 212 to deactivate ozone reduction chamber 121 (e.g., turning off fan 123 and closing intake port 124 and exhaust port 126.)

FIG. 7 illustrates a flow chart of an example method for implementing an open cycle 700. Open cycle 700 can be implemented when ozone concentration is below the threshold and/or at safe level. Open cycle 700 includes turning off ozone monitors (701). For example, controller 131 can send one or more of output signals 212 to the UV sensors(s) in disinfection chamber 102 to turn off the UV sensor(s). Open cycle 700 includes venting vacuum gaps (702). For example, controller 131 can send one or more of output signals 212 to vent components (not shown) at container 100. The output signals 212 can instruct the vent components to vent atmosphere into the gap between the individual seals (of the drawer/door at container 100) through the vacuum/vent port. The output signals 212 can also instruct the vent components to vent atmosphere into gaps of any other double chamber seals at container 100.

Opening cycle 700 includes deflating seals (703). For example, controller 131 can send one or more of output signals 212 to sealing components of container 100. The output signals can instruct the sealing components to deflate individual seals of the double chamber seal of the drawer/door at container 100. The output signals 212 can instruct the sealing components to deactivate other seals, for example, at vents, access points, intake ports 114 and 124, exhaust ports 116 and 126, etc. when appropriate.

Opening cycle 700 includes displaying a "complete" message (704). For example, controller 131 can activate an "complete" light indicator on container 100 and/or indicate at information screen 202 that disinfection of medical article 103 is complete. Opening cycle 700 includes unlocking a drawer/door (705). For example, controller 131 can send one or more of output signals 212 to unlock the drawer/door of container 100. Medical article 103 can then be removed from container 100.

Status Indicators

Controller 131 can indicate variety of disinfection state information using status lights at container 100 and/or colors at information screen 202. Blue can indicate that contents of container 100 are currently undergoing a disinfection/sterilization cycle and that the container 100 is locked and cannot be opened. White or clear can indicated can indicate that container 100 is empty. Yellow can indicates that container 100 is occupied, and that container 100 has been opened and accessed since the last disinfection/sterilization cycle. Green can indicate that the contents of container have undergone a disinfection/sterilization cycle and that the container 100 has not been opened since the cycle was completed.

Figure 8:
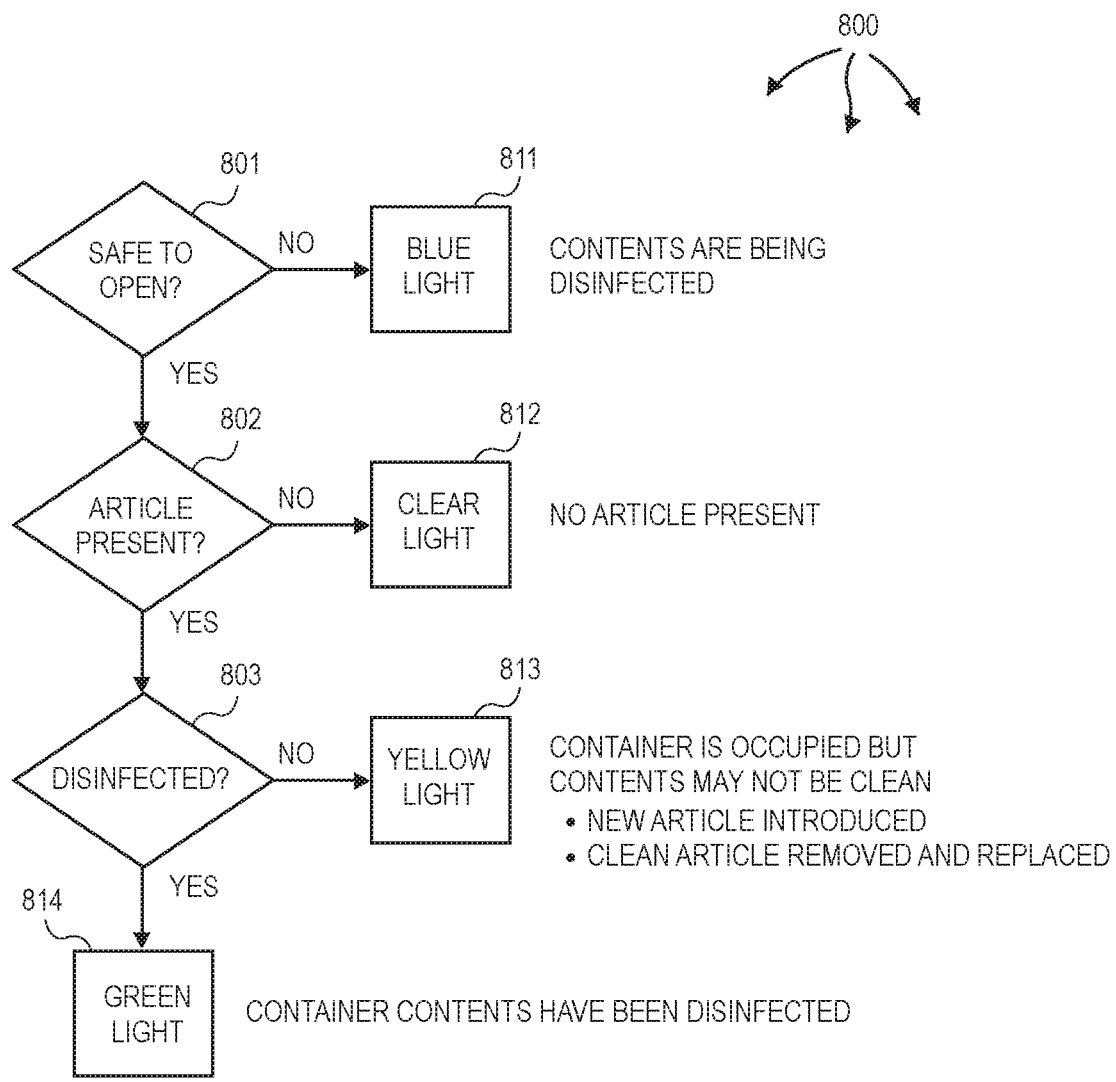
FIG. 8 illustrates a data flow of example status and status indictors for a disinfection container.

FIG. 8 illustrates a data flow 800 of example status and status indictors for a disinfection container. At decision block 801, controller 131 can inform an operator of container 100 if container 100 is safe to open (e.g., ozone concentration is at a safe level) (801). Controller 131 can illuminate blue light 811 to indicate that the contents of container 100 are being disinfected and container 100 is not safe to open. When blue light 811 is not illuminated, container 100 is safe to open. Controller 131 can also inform the operator if an article is present in container 100 (802). A sensor, such as, a pressure sensor, can be used to detect an article. Controller 131 can illuminate clear light 812 to indicate that container 100 does not contain an article.

If container 100 does contain an article, controller 131 can also inform the user if the article is disinfected (803). Controller 131 can illuminate yellow light 812 to indicate that an article may not be disinfected. For example, an additional article may have been introduced into container 100 since a disinfection cycle completed or a disinfected article may have been removed and replaced into container 100. Controller 131 can illuminate green light 812 to indicate that an article is disinfected.

Alternately or in combination, controller 131 can display similar indications at information screen 202 (e.g., a graphical user interface).

Handling Power Disruptions

In some environments, container 100 is connected to a facility uninterruptable power source (UPS). The facility UPS can be connected to generators and/or significant battery backup resources. As such, the likelihood of power disruption at container 100 is significantly reduced. However, in other environments, container 100 is not connected to a facility UPS. In these other environments, as well as during extend outages (even when connected to a facility UPS), power disruptions at container 100 can occur.

Figure 9:
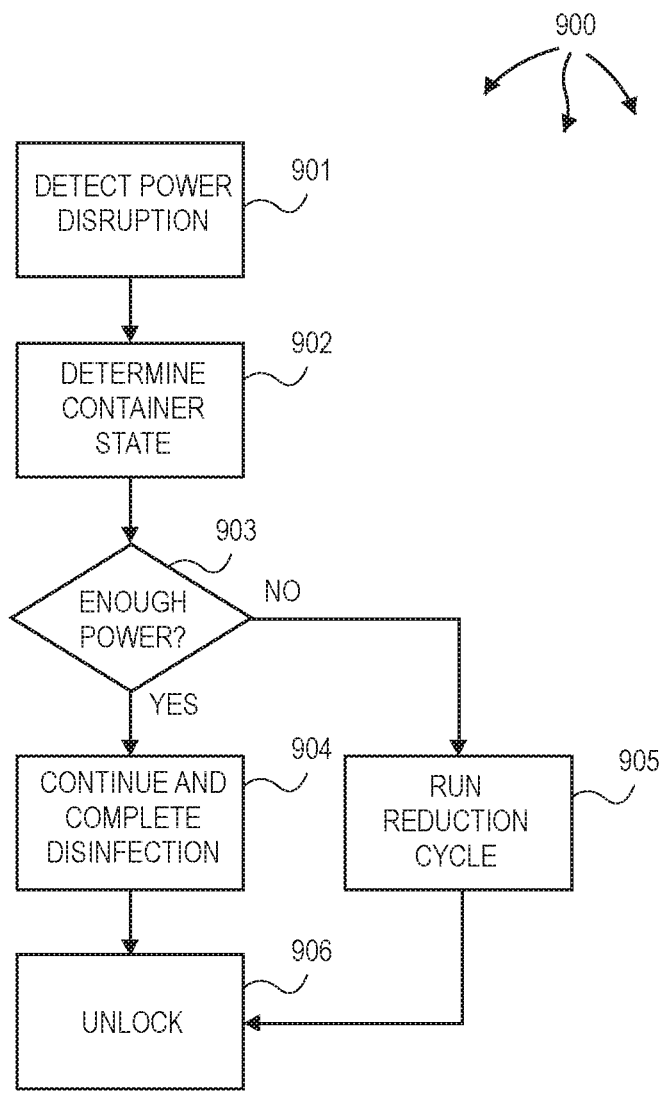
FIG. 9 illustrates a flow chart of an example method for addressing power disruption at a disinfection container.

UPS 132 can be plugged into a wall socket (mains power). Batteries in UPS 132 can be charged. When mains power is disrupted, the batteries can power components of container 100 for an amount of time (e.g., 10 minutes) sufficient to transition container 100 to a safe state (e.g., ozone concentration inside disinfection chamber 102 <50 ppba). FIG. 9 illustrates a flow chart of an example method for 900 addressing power disruption at a disinfection container.

Method 900 includes detecting a power disruption (901). For example, UPS 132 can detect a power disruption in mains power (e.g., a black out, brown out, a spike, etc.). Method 900 includes determining container state (902). For example, controller 131 can determine the state of container 100, such as, for example, "in operation", "idle", "disinfected", "sterilized", etc. Method 900 includes calculating if there is enough power to complete disinfection based on the determined state (903). For example, controller 131 can calculate if UPS 132 contains sufficient power to complete remaining cycles for disinfecting medical article 103 at container 100.

If not (NO at 903), method 900 includes running a reduction cycle (905). For example, when UPS 132 lacks sufficient power to complete disinfecting medical article 103, controller 131 can transition container 100 to a reduction cycle (e.g., similar to reduction cycle 600). The reduction cycle can reduce ozone concentrations in container 100 below a threshold and/or to safe levels before the power in UPS 132 is exhausted.

If so, (YES at 903), method 900 includes continuing and completing disinfection (904). For example, when UPS 132 contains sufficient power to complete disinfecting medical article 103, controller 131 allows a current cycle and any subsequent cycles to continue at container 100. Method 900 includes unlocking the container (906). For example, controller 131 can unlock container 100.

Controller 131 and/or UPS 132 can implement other safety measures to prevent container 100 from starting disinfection/sterilization when mains power is not available. After a power outage, controller 131 can require container 100 to run through a disinfection/sterilization cycle upon power being restored (unless an authorized user bypasses this action).

Supply Carts

In many healthcare environments, supply carts containing various medical articles are stored within patient rooms. During storage in a supply cart, the medical articles can remain enclosed in their protective packaging. However, the packaging has some exposure to pathogens through airborne or contact transmission. For example, pathogens may be transferred to the packaging via respiratory droplets when a drawer or door is opened, via direct contact with a person's contaminated hand or glove when removing a medical article, etc. Thus, packaged medical articles in a supply cart can be considered contaminated even if medical articles have not been removed from the supply cart or their protective packaging.

Use of contaminated medical articles is particularly problematic in isolation units where additional care is given to prevent a patient from being exposed to another patient's pathogens. Thus, unused, potentially contaminated packaged medical articles are often disposed of to reduce pathogen transfer between patients. However, disposal of unused medical articles is costly.

In one aspect, the contents of a healthcare supply cart are disinfected and/or sterilized using ozone. Since ozone is a gas, essentially all surfaces within the healthcare supply cart are subject to impinging ozone molecules through diffusion mechanisms (e.g., governed by concentration gradients) and/or forced recirculation. As such, external and internal surfaces in an open pathway between an ozone source and the surface can be disinfected and/or sanitized.

Figure 10:
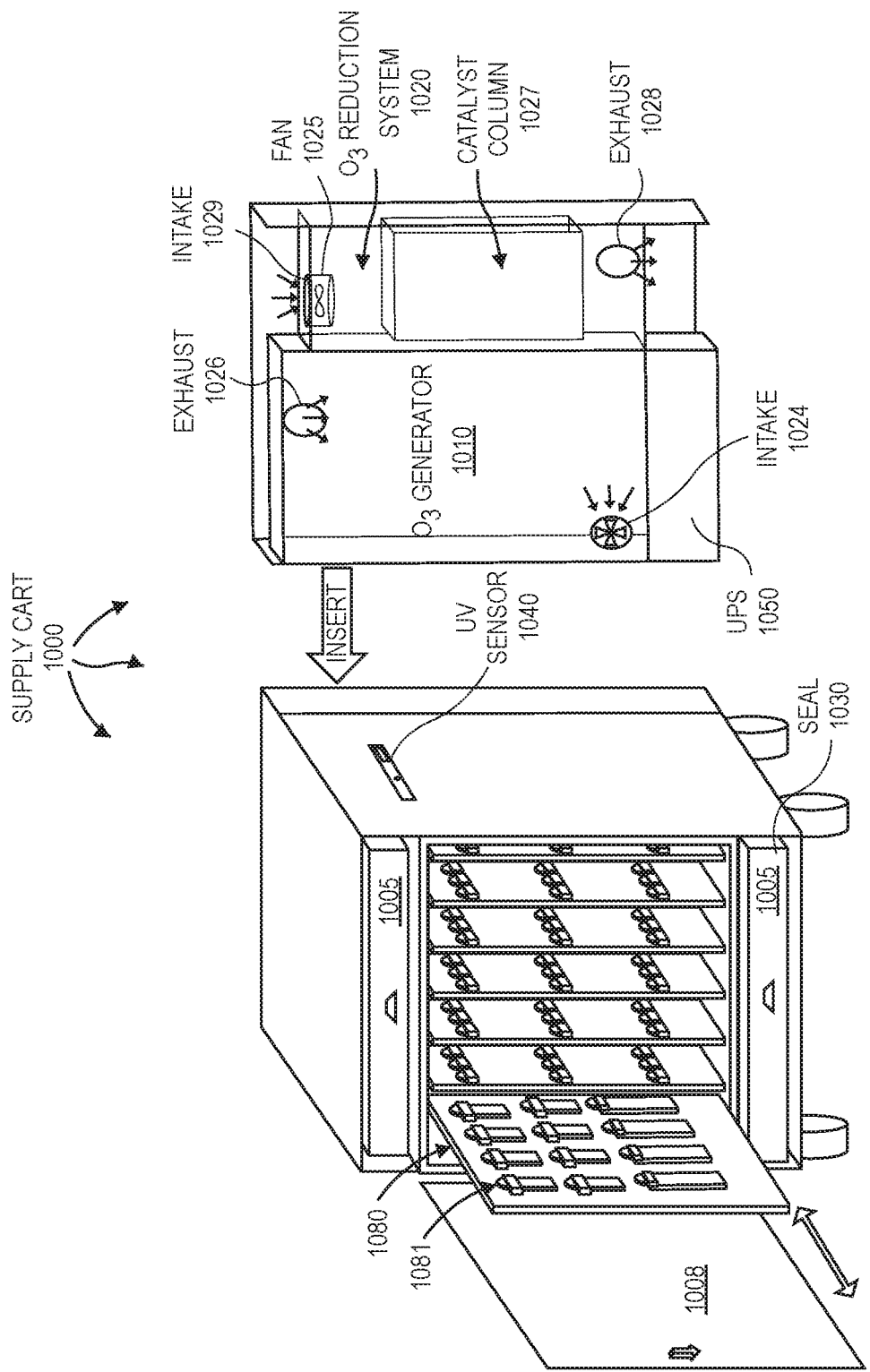
FIG. 10 illustrates an example supply cart.

FIG. 10 illustrates an example supply cart 1000. Supply cart 1000 can hold supplies used in healthcare facilities or other facilities that require supplies to be disinfected or sterilized. The body of supply cart 1000 includes a plurality of drawers 1005 and/or doors 1008 providing access to compartments inside. Supply cart 1000 can contain a plurality of vertical supply boards 1080. Each supply board 1080 can include one or more clips 1081, pegs, or hooks, used to hang supplies.

Supply cart 1000 can also include a controller (not shown, possibly similar to controller 131). The controller can control the components of supply cart 1000 to disinfect and/or sterilize medical articles contained therein. In one aspect, the controller facilitates a preparation cycle, a disinfection/sterilization cycle, a reduction cycle, and an open cycle. Supply cart 1000 can also include indicator lights and/or an information screen. The controller can use the indicator lights and/or information screen to indicate the status of supply cart 1000.

Supply cart 1000 also includes on-board ozone generator 1010. Ozone generator 1010 includes a fan at intake 1024. The fan can force circulation of atmosphere from inside supply cart 1000 (air and ozone) through intake 1024, through ozone generator 1010, and back through exhaust 1026 to the atmosphere inside supply cart 1000. The fan also forces movement of ozone throughout the inside of supply cart 1000 to optimize ozone exposure to surfaces. The fan can force atmosphere inside supply cart 1000 to pass through ozone generator 1010 multiple times within the natural half-life of ozone. As such, relatively high concentrations of ozone can be achieved in a short period of time.

Supply cart 1000 also includes ozone reduction system 1020. Ozone reduction system 1020 can contain a hollow vertical tube (e.g., cylindrical or polygonal in cross section) open on both ends. Ozone reduction system 1020 contains catalyst column 1027, including $MnO_2$ or other suitable catalyst, to convert ozone into Oxygen ($O_2$). The top opening is intake 1029 and adjacent fan 1025. Intake 1029 includes a louver that can seal off intake 1029. Fan 1025 can be turned on to draw ozone from inside supply cart 1000 into ozone reduction system 1020.

Ozone reduction system 1020 can hold catalyst column 1027 in place with a stainless steel (or other ozone compatible material) mesh. Ozone can be forced through the mesh by fan 1025, converting the ozone to Oxygen ($O_2$), and expelling the Oxygen ($O_2$) through exhaust 1028 back into the inside supply cart 1000. The amount of catalyst (e.g., $MnO_2$) and the velocity at which the ozone flows through the catalyst determines how quickly ozone is converted to Oxygen ($O_2$). Supply cart 1000 and ozone reduction system 1020 can be configured so that ozone reduction happens in a single pass or multiple passes.

The inside of supply cart 1000 can also include multiple ozone sensors. An ultra-violet (UV) absorption sensor 1040 can continuously monitor and determine the concentration of ozone inside supply cart 1000. UV absorption sensor 1040 can include a light emitting diode and a photodiode. The light emitting diode can be configured to emit light of a specified wavelength and the photodiode can be configured to detect light of the specified wavelength. In one aspect, the light emitting diode is configured to emit and the photodiode is configured to detect light having a wavelength between 240 nm-260 nm (i.e., 250 nm, +/−10 nm). In another aspect, the light emitting diode is configured to emit and the photodiode is configured to detect light having a wavelength between 250 nm-260 nm (i.e., 255 nm, +/−5 nm).

The UV light from the emitter is absorbed by the ozone in the atmosphere, therefore, the amount of light detected by the photodiode is dependent upon the amount of ozone inside supply cart 1000. As described, UV absorption sensor 1040 can be used determine when ozone is present inside of supply cart 1000 and at what level. Thus, UV absorption sensor 1040 can also be used for disinfection/sterilization endpoint determination and to determine when it is safe to open supply cart 1000.

Supply cart 1000 includes UPS 1050. UPS 1050 can perform any of the operations described with respect to UPS 132.

Figure 11B:
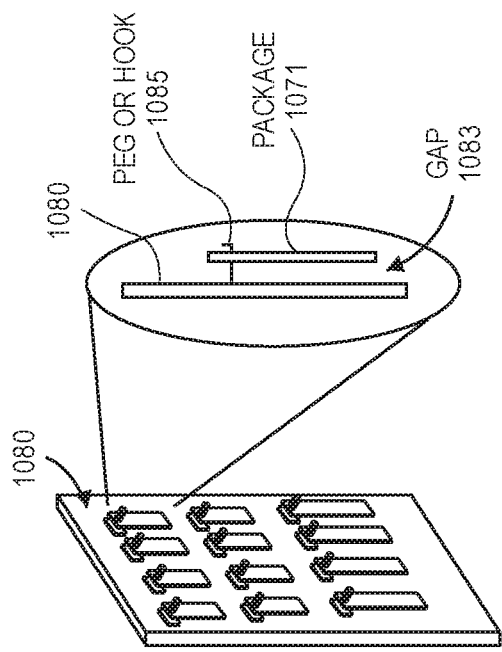
FIG. 11B illustrates an example supply board including a plurality of pegs or hooks.
Figure 11C:
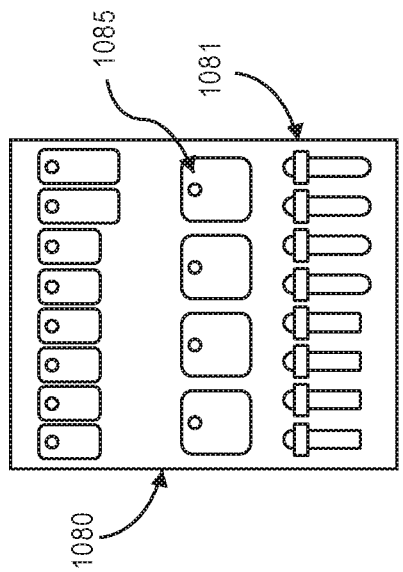
FIG. 11C illustrates an example supply board including a plurality of pegs or hooks and a plurality of clips.
Figure 11A:
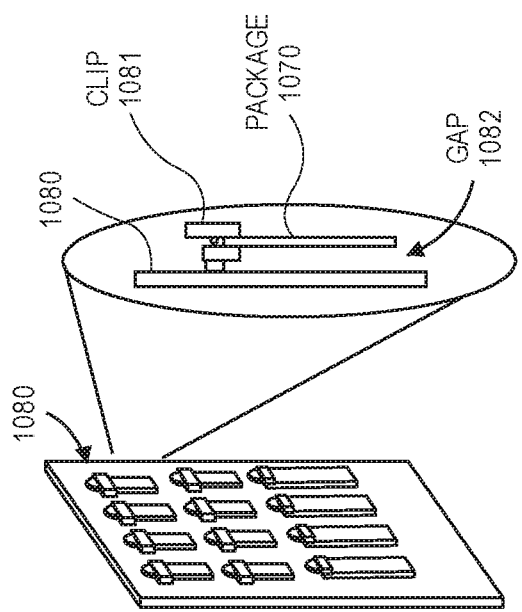
FIG. 11A illustrates an example supply board including a plurality of clips.

In general, FIGS. 11A-11C illustrate examples of holding articles (e.g., packaged medical supplies) in place on a vertical supply board 1080. Vertical supply board 1080 can be perforated to allow ozone to travel freely in the environment. Vertical supply board 1080 is configured to slide into and out of supply cabinet 1000 allowing easy access to supplies. Vertical supply board 1080 can be constructed from any of a variety of different materials including, but not limited, to a wire mesh, a perforated metal plate, or a perforated plastic plate.

Different mechanisms can be used to hold articles in place on vertical supply board 1080. FIG. 11A illustrates vertical supply board 1080 including a plurality of (e.g., spring loaded) clips 1081. FIG. 11B illustrates vertical supply board 1080 including a plurality of pegs or hooks 1085. If packaged supplies do not include a mounting hole, clip 1081 can be used to hold the packaged supplies. For example, clip 1081 can be opened, package 1070 inserted, and clip 1081 can be closed. On the other hand, if packaged supplies do include a mounting hole, then a peg or hook 1085 can be used to hold the packaged supplies. For example, a mounting hole on package 1071 can be placed over peg or hook 1085.

Clips 1081 can be constructed from an ozone compatible material. Clips 1081 can have sufficient clamping force to hold the weight of package 1070 and can be opened and closed many (e.g., thousands or more) times without failure. Clips 1081 are configured so that package 1070 hangs freely with gap 1082 maintained between package 1070 and vertical supply board 1080. Gap 1082 allows ozone between vertical supply board 1080 and package 1070, increasing package 1070's ozone exposure.

Likewise, pegs or hooks 1085 can be constructed from an ozone compatible material. Pegs or hooks 1085 can be sized to permit a mounting hole of package 1071 to slide over the peg or hook. Pegs or hooks 1085 can include an obstruction to prevent the package 1071 from sliding off inadvertently. Pegs or hooks 1085 are configured so that package 1071 hangs freely with gap 1083 maintained between package 1071 and vertical supply board 1080. Gap 1083 allows ozone between vertical supply board 1080 and package 1071, increasing package 1071's ozone exposure.

A vertical supply board can contain a plurality of clips and a plurality pegs or hooks as well as a mixture of clips and pegs or hooks. FIG. 11C illustrates vertical supply board 1080 including a plurality of pegs or hooks 1085 and a plurality of clips 1081. Packages/supplies can be mounted on either or both sides of vertical supply board 1080.

Figure 12A:
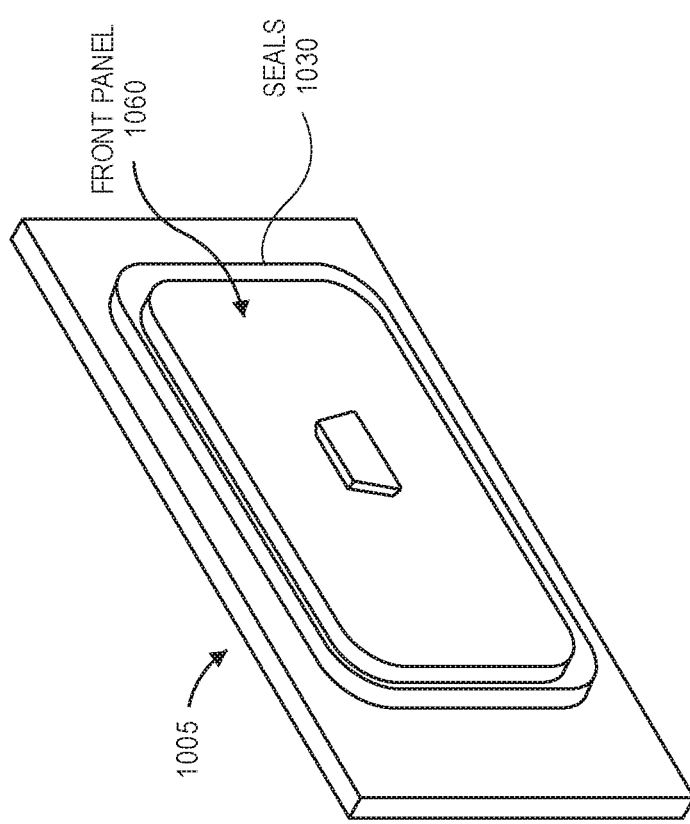
FIG. 12A illustrates an example front portion of an example drawer.

In general, FIGS. 12A-12D illustrate example drawer features. More specifically, FIG. 12A illustrates a front portion of a drawer 1005. As depicted, drawer 1005 includes front panel 1060 and pair of expanding (e.g., inflatable) seals 1030. Front panel 1060 is configured to allow close and direct contact between inflatable, expandable seals 1030 and other parts of drawer 1005 and supply cart 1000 when seals 1030 are inflated.

The controller can inflate seals 1030 prior to articles inside supply cart 1000 being disinfected and can maintain inflation during disinfection (e.g., during a disinfection/sterilization cycle). When inflated, seals 1030 prevent atmosphere (and thus ozone) inside drawer 1005 from escaping outside of supply cart 1000. Seals 1030 can remain deflated when supply cart 1000 is not being used for disinfecting. When deflated, seals 1030 retract and do not contact with other components of drawer 1005. As such, wear on seals 1030 is reduced when drawer 1005 is opened and closed. Similar inflatable, expanding seals can be used on door 1008 to prevent atmosphere (and thus ozone) from escaping outside of supply cart 1000.

A vacuum/vent port (not shown) can be included in a gap between the pair of expanding seals 1030. The vacuum/vent port can be used to evacuate atmosphere from the gap (e.g., during a preparation cycle) and vent atmosphere into the gap (e.g., during an open cycle). The gap between the pair of expanding seals can also be monitored for leaks during disinfection. If ozone is detected in the gap, supply cart 1000 can perform a shutdown, including transitioning to a reduction cycle (possibly prior to complete disinfection).

Figure 12B:
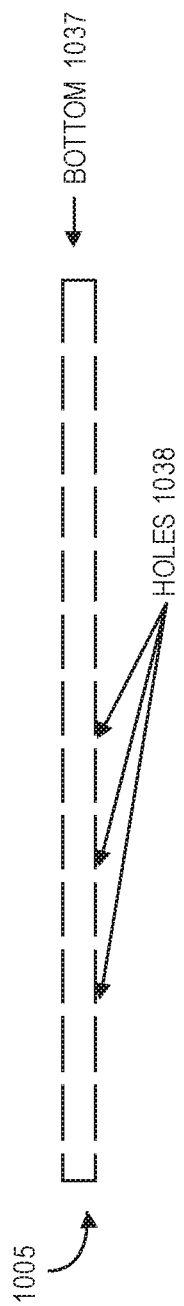
FIG. 12B illustrates an example bottom portion of an example drawer.

FIG. 12B illustrates a bottom portion 1037 of a drawer 1005. As depicted, bottom portion 1037 is perforated with holes 1038 to allow the free flow of ozone into drawer 1005. Drawer 1005 can also be equipped with a vibration mechanism that shifts the articles contained in drawer 1005. Shifting the contents facilitates increased exposure of surfaces in drawer 1005 to ozone atmosphere. In other aspects, articles contained in drawer 1005 are moved physically to increase surface exposure to ozone.

Figure 12C:
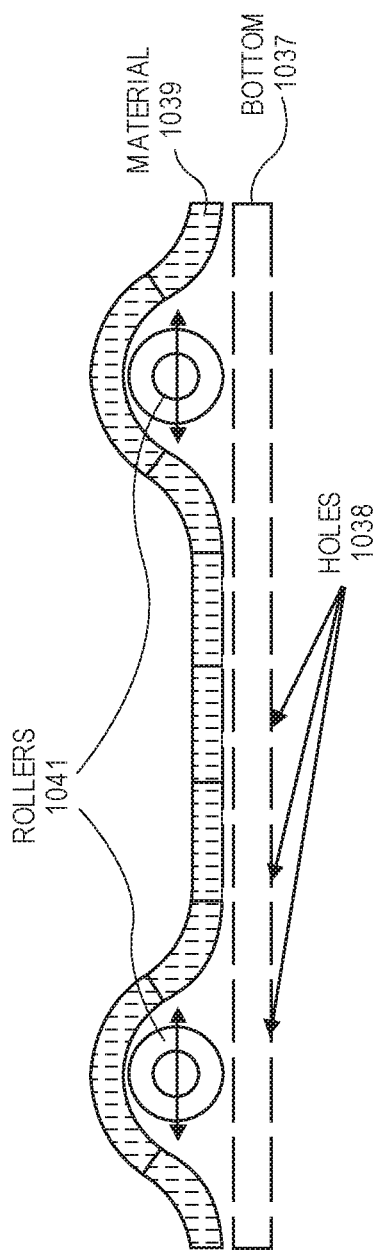
FIG. 12C illustrates another example bottom portion of an example drawer

FIG. 12C illustrates another example bottom portion of an example drawer 1005. As depicted, a flexible, porous material 1039 is placed on top of rollers 1041. The controller can move rollers 1041 move back and forth undulating material 1039 up and down. The undulation causes any articles in drawer 1005 to change positions relative to one another. As articles change positions, surface exposure to ozone atmosphere is increased.

Figure 12D:
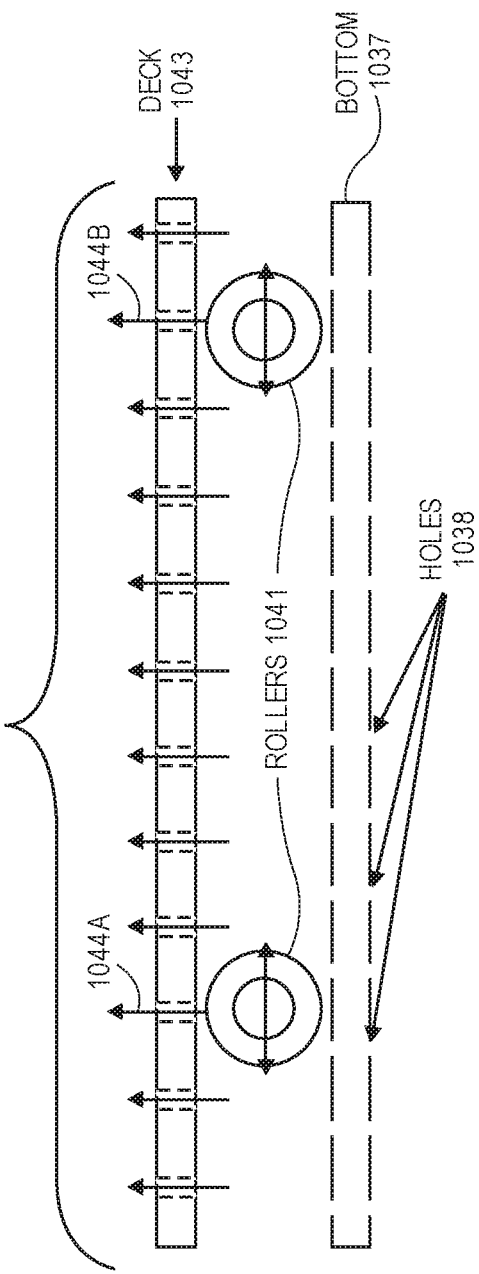
FIG. 12D illustrates a further example bottom portion of an example drawer

FIG. 12D illustrates a further example bottom portion of an example drawer. As depicted, deck 1043 is configured above rollers 1041 and includes lift pins 1044. The controller can move rollers 1041 move back and forth causing lift pins 1044 to lift and drop as rollers make and lose contact with lift pins 1044. For example, as depicted, rollers 1041 are in contact with pins 1044A and 1044B causing pins 1044A and 1044B to lift. As pins lift and drop, the pins can make contact with articles contained in drawer 1005 causing the articles to change positions relative to one another. As articles change positions, surface exposure to ozone atmosphere is increased.

Garment Disinfection Cabinet

In many healthcare environments, various pieces of clothing, including wearable surgical vestments, x-ray aprons, etc. are worn by healthcare providers as well as patients. The clothing can be exposed to pathogens through airborne or contact transmission. For example, pathogens may be transferred to clothing via respiratory droplets, via direct contact with contaminated surface, etc. Thus, clothing can be considered contaminated after a relatively short period of time in use. Use of contaminated clothing is particularly problematic in isolation units where additional care is given to prevent a patient from being exposed to another patient's pathogens.

In one aspect, clothing articles are placed in a garment disinfection cabinet and disinfected and/or sterilized using ozone. Since ozone is a gas, essentially all surfaces within the garment disinfection cabinet are subject to impinging ozone molecules through diffusion mechanisms (e.g., governed by concentration gradients) and/or forced recirculation. As such, external and internal surfaces in an open pathway between an ozone source and the surface can be disinfected and/or sanitized.

Figure 13A:
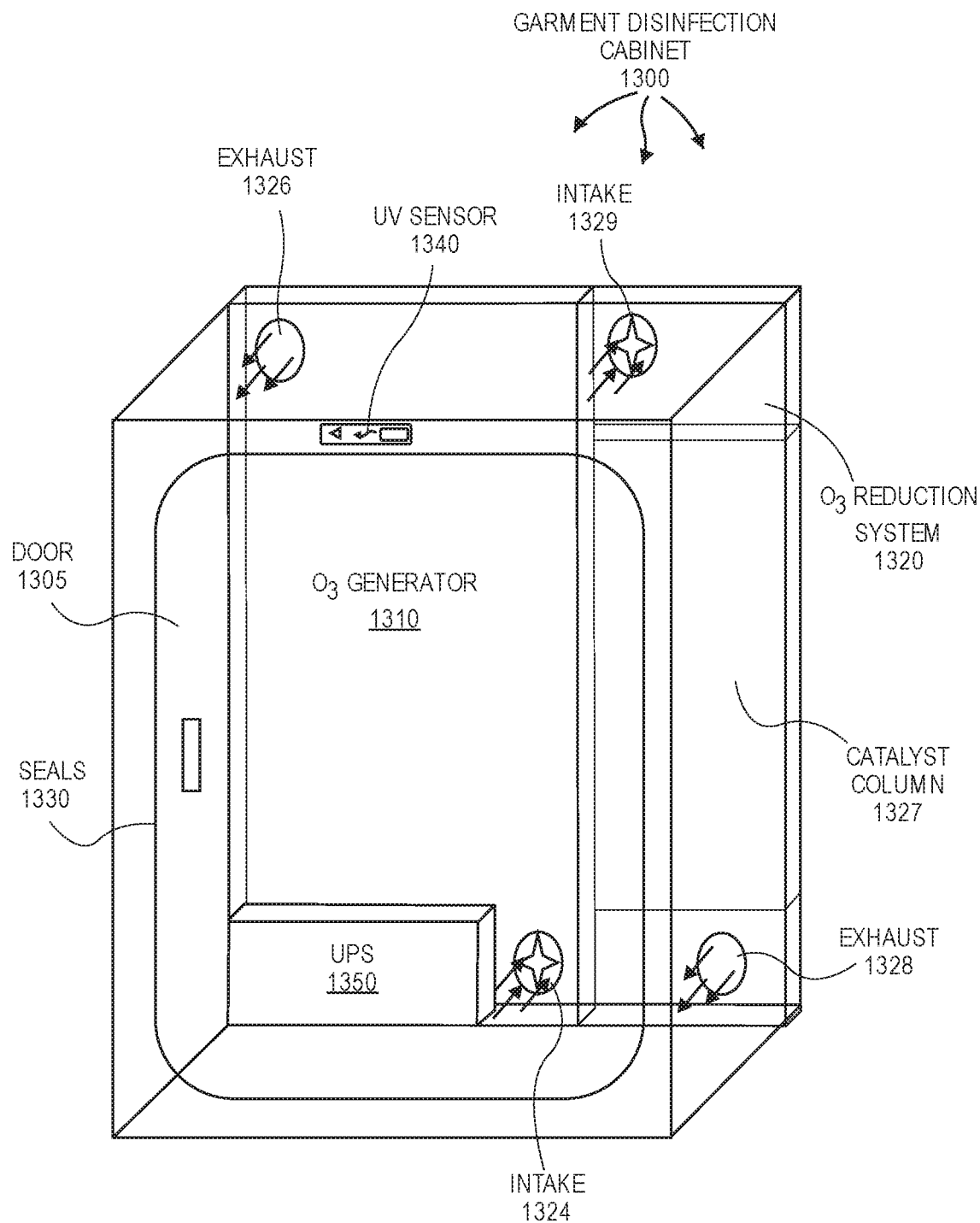
FIG. 13A illustrates an example garment disinfection cabinet.

FIG. 13A illustrates an example garment disinfection cabinet 1300. Garment disinfection cabinet 1300 can include a plurality of doors and/or drawers 1305 providing access to compartments inside garment disinfection cabinet 1300. Garments and supplies, such as, x-ray aprons worn by healthcare personnel and/or patients, can be placed in compartments of disinfection cabinet 1300. In one aspect, garment disinfection cabinet 1300 is sized to hold one or more x-ray aprons.

Garment disinfection cabinet 1300 can also include a controller (not shown, possibly similar to controller 131). The controller can control the components of garment disinfection cabinet 1300 to disinfect and/or sterilize medical articles contained therein. In one aspect, the controller facilitates a preparation cycle, a disinfection/sterilization cycle, a reduction cycle, and an open cycle. Garment disinfection cabinet 1300 can also include indicator lights and/or an information screen. The controller can use the indicator lights and/or information screen to indicate the status of garment disinfection cabinet 1300.

Garment disinfection cabinet 1300 includes ozone generator 1310. Ozone generator 1310 includes a fan at intake 1324. The fan can force circulation of atmosphere from garment disinfection cabinet 1300 (air and ozone) through intake 1324, through ozone generator 1310, and back through exhaust 1326 to the atmosphere inside garment disinfection cabinet 1300. The fan also forces movement of ozone throughout the inside of garment disinfection cabinet 1300 to optimize ozone exposure to surfaces. The fan can force atmosphere inside garment disinfection cabinet 1300 to pass through ozone generator 1310 multiple times within the natural half-life of ozone. As such, relatively high concentrations of ozone can be achieved in a short period of time.

Garment disinfection cabinet 1300 also includes ozone reduction system 1320. Ozone reduction system 1320 can contain a hollow vertical tube (e.g., cylindrical or polygonal in cross section) open on both ends. Ozone reduction system 1320 contains catalyst column 1327, including $MnO_2$ or other suitable catalyst to convert ozone in into Oxygen ("$O_2$"). The top opening is intake 1329 and adjacent fan. Intake 1329 includes a louver that can seal off intake 1329. The fan can be turned on to draw ozone from inside garment disinfection cabinet 1300 into ozone reduction system 1320.

Ozone reduction system 1320 can hold catalyst column 1327 in place with a stainless steel (or other ozone compatible material) mesh. Ozone can be forced through the mesh by the fan, converting the ozone to Oxygen ($O_2$), and expelling the Oxygen ($O_2$) through exhaust 1328 back into the inside of garment disinfection cabinet 1300. The amount of catalyst (e.g. $MnO_2$) and the velocity at which the ozone flows through the catalyst determines how quickly ozone is converted to Oxygen ($O_2$). Garment disinfection cabinet 1300 and ozone reduction system 1320 can be configured so that ozone reduction happens in a single pass or multiple passes.

The inside of garment disinfection cabinet 1300 can also include multiple ozone sensors. An ultra-violet (UV) absorption sensor 1340 can continuously monitor and determine the concentration of ozone in the garment disinfection cabinet 1300. UV absorption sensor 1340 can include a light emitting diode and a photodiode. The light emitting diode can be configured to emit light of a specified wavelength and the photodiode can be configured to detect light of the specified wavelength. In one aspect, the light emitting diode is configured to emit and the photodiode is configured to detect light having a wavelength between 240 nm-260 nm (i.e., 250 nm, +/−10 nm). In another aspect, the light emitting diode is configured to emit and the photodiode is configured to detect light having a wavelength between 250 nm-260 nm (i.e., 255 nm, +/−5 nm).

The UV light from the emitter is absorbed by the ozone in the atmosphere, therefore, the amount of light detected by the photodiode is dependent upon the amount of ozone in the environment. As described, UV absorption sensor 1340 can be used determine when ozone is present inside of garment disinfection cabinet 1300 and at what level to ensure safe operation. UV absorption sensor 1340 can also be used for endpoint determination and to determine when it is safe to open garment disinfection cabinet 1300.

Garment disinfection cabinet 1300 includes UPS 1350. UPS 1350 can perform any of the operations described with respect to UPS 132.

Cabinet door 1305 can include a pair of expanding (inflatable) seals 1330 to prevent ozone from escaping inside garment disinfection cabinet 1300. A front panel of cabinet door 1305 can be configured to allow close and direct contact between inflatable, expandable seals 1330 and other parts of door 1305 and garment disinfection cabinet 1300 when seals 1330 are inflated.

The controller can inflate seals 1330 prior to articles inside garment disinfection cabinet 1300 being disinfected and can maintain inflation during disinfection (e.g., during a disinfection/sterilization cycle). When inflated, seals 1330 prevent atmosphere (and thus ozone) inside garment disinfection cabinet 1300 from escaping outside of garment disinfection cabinet 1300. Seals 1330 can remain deflated when garment disinfection cabinet 1300 is not being used for disinfecting. When deflated, seals 1330 retract and do not contact with other components of door 1305. As such, wear on seals 1330 is reduced when door 1305 is opened and closed. Similar inflatable, expanding seals can be used on any other doors and/or drawers of garment disinfection cabinet 1300 to prevent atmosphere (and thus ozone) from escaping outside of garment disinfection cabinet 1300.

A vacuum/vent port (not shown) can be included in a gap between the pair of expanding seals 1330. The vacuum/vent port can be used to evacuate atmosphere from the gap (e.g., during a preparation cycle) and vent atmosphere into the gap (e.g., during an open cycle). The gap between the pair of expanding seals can also be monitored for leaks during disinfection. If ozone is detected in the gap, garment disinfection cabinet 1300 can perform a shutdown, including transitioning to a reduction cycle (possibly prior to complete disinfection).

Figure 13B:
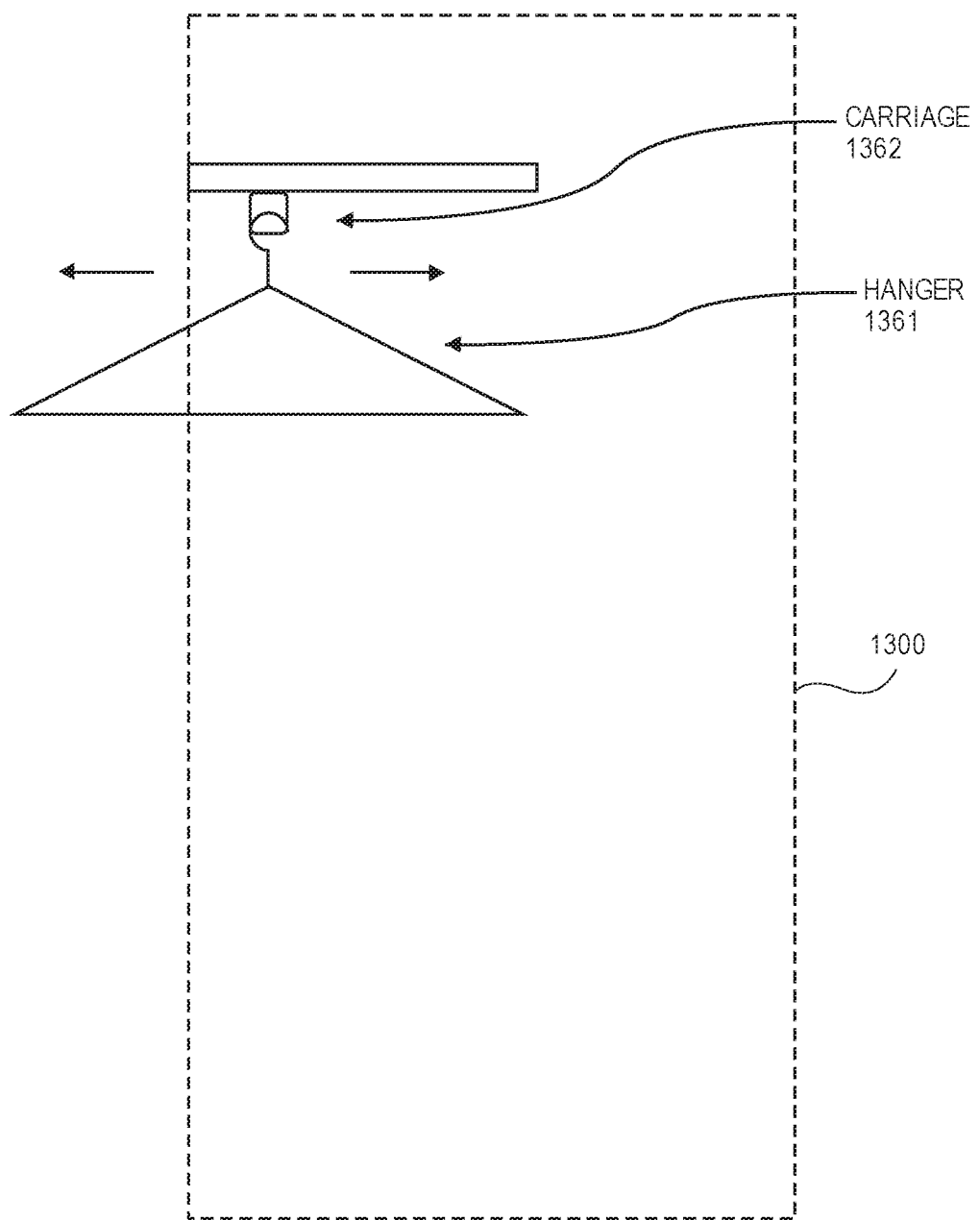
FIG. 13B illustrates an example hanger system inside a garment disinfection cabinet.

FIG. 13B illustrates an example hanger system inside garment disinfection cabinet 1300. As depicted, hanger 1361 is connected to carriage 1362. A garment can be placed on hanger 1361 for disinfection (e.g., through a disinfection/ sterilization cycle). Carriage 1362 can glide in and out of the cabinet framer, for improved access when loading and unloading the garment. An operator can control carriage 1362 using any of variety of options, including, but not limited to voice-commands, foot trigger, badge scan, facial recognition, and/or motion sensing, so that the operator does not have to contact the outside of garment disinfection cabinet 1300.

A garment can hang freely within garment disinfection cabinet 1300. Hangers can be spaced so that there are gaps between adjacent garments and/or gaps between garments and the walls of garment disinfection cabinet 1300. The gaps allow ozone between adjacent garments and between garments and the walls, increasing garments' ozone exposure.

Disinfection Tumbler

In many healthcare environments, there are also bulkier medical articles or medical articles that are otherwise incompatible with other cleaning methods, such as, washers and dryers. In one aspect, bulkier (as well as other articles) are placed in a disinfection tumbler and disinfected and/or sterilized using ozone. Since ozone is a gas, essentially all surfaces within the garment disinfection cabinet are subject to impinging ozone molecules through diffusion mechanisms (e.g., governed by concentration gradients) and/or forced recirculation. As such, external and internal surfaces in an open pathway between an ozone source and the surface can be disinfected and/or sanitized.

Figure 14A:
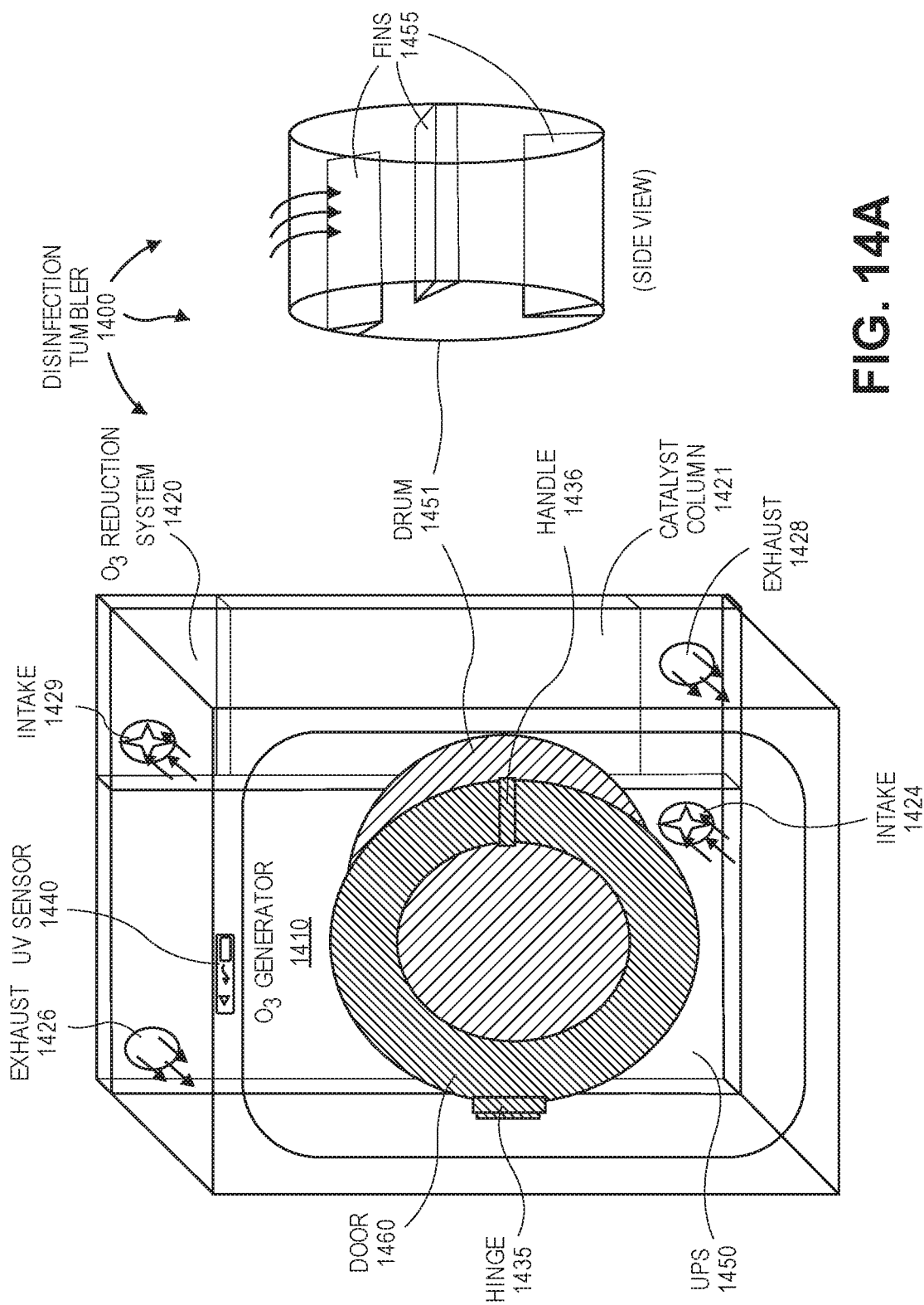
FIG. 14A illustrates an example disinfection tumbler in a closed configuration.

FIG. 14A illustrates disinfection tumbler 1400 in a closed configuration. Disinfection tumbler 1400 includes door 1460 having (e.g., articulated) hinge 1435 and (e.g., latching) handle 1436. Door 1450 provides access to (internal) drum 1451 (or another rotating chamber). A side view of drum 1451 (or other rotating chamber) also depicts fins 1455. Door 1460 can be opened and articles from healthcare facilities or other facilities placed into drum 1451 for disinfection.

Disinfection tumbler 1400 can also include a controller (not shown, possibly similar to controller 131). The controller can control the components of disinfection tumbler 1400 to disinfect and/or sterilize medical articles contained therein. In one aspect, the controller facilitates a preparation cycle, a disinfection/sterilization cycle, a reduction cycle, and an open cycle. Disinfection tumbler 1400 can also include indicator lights and/or an information screen. The controller can use the indicator lights and/or information screen to indicate the status of disinfection tumbler 1400.

After loading, the controller can rotate drum 1451 in the range of 0.5 to 10 revolutions per minute. Rotating drum 1451 causes articles in drum 1451 to contact fins 1455 and change positions relative to one another. The (relatively slower) rotational speed of drum 1451 also prevents articles from being pinned to the walls of drum 1451 due to rotational forces. As articles change positions, surface exposure to ozone atmosphere is increased. The (relatively slower) rotational speed of drum 1451 also minimizes damage to articles and packaging. The walls of drum 1451 can be perforated to permit free flow of ozone into drum 1451.

Disinfection tumbler 1400 includes ozone generator 1410. Ozone generator 1410 includes a fan at intake 1424. The fan can force circulation of atmosphere from garment disinfection cabinet 1400 (air and ozone) through intake 1424, through ozone generator 1410, and back through exhaust 1426 to the atmosphere inside disinfection tumbler 1400. The fan also forces movement of ozone throughout the inside of drum 1451 to optimize ozone exposure to surfaces. The fan can force atmosphere inside disinfection tumbler 1400 to pass through ozone generator 1410 multiple times within the natural half-life of ozone. As such, relatively high concentrations of ozone can be achieved in a short period of time.

Disinfection tumbler 1400 also includes ozone reduction system 1420. Ozone reduction system 1420 can contain a hollow vertical tube (e.g., cylindrical or polygonal in cross section) open on both ends. Ozone reduction system 1420 contains catalyst column 1427, including $MnO_2$ or other suitable catalyst to convert ozone in into Oxygen ($O_2$). The top opening is intake 1429 and adjacent fan. Intake 1429 includes a louver that can seal off intake 1429. The fan can be turned on to draw ozone from inside disinfection tumbler 1400, including drum 1451, into ozone reduction system 1420.

Ozone reduction system 1420 can hold catalyst column 1427 in place with a stainless steel (or other ozone compatible material) mesh. Ozone can be forced through the mesh by the fan, converting the ozone to Oxygen ($O_2$), and expelling the Oxygen ($O_2$) through exhaust 1428 back into the inside of disinfection tumbler 1400. The amount of catalyst (e.g., $MnO_2$) and the velocity at which the ozone flows through the catalyst determines how quickly ozone is converted to Oxygen ($O_2$). Disinfection tumbler 1400 and ozone reduction system 1420 can be configured so that ozone reduction happens in a single pass or multiple passes.

The inside of disinfection tumbler 1400 can also include multiple ozone sensors. An ultra-violet (UV) absorption sensor 1440 can continuously monitor and determine the concentration of ozone in the disinfection tumbler 1400. UV absorption sensor 1440 can include a light emitting diode and a photodiode. The light emitting diode can be configured to emit light of a specified wavelength and the photodiode can be configured to detect light of the specified wavelength. In one aspect, the light emitting diode is configured to emit and the photodiode is configured to detect light having a wavelength between 240 nm-260 nm (i.e., 250 nm, +/−10 nm). In another aspect, the light emitting diode is configured to emit and the photodiode is configured to detect light having a wavelength between 250 nm-260 nm (i.e., 255 nm, +/−5 nm).

The UV light from the emitter is absorbed by the ozone in the atmosphere, therefore, the amount of light detected by the photodiode is dependent upon the amount of ozone in the environment. As described, UV absorption sensor 1440 can be used determine when ozone is present inside of disinfection tumbler 1400 and at what level to ensure safe operation. UV absorption sensor 1440 can also be used for endpoint determination and to determine when it is safe to open garment disinfection tumbler 1400.

Disinfection tumbler 1400 includes UPS 1450. UPS 1450 can perform any of the operations described with respect to UPS 142.

Figure 14B:
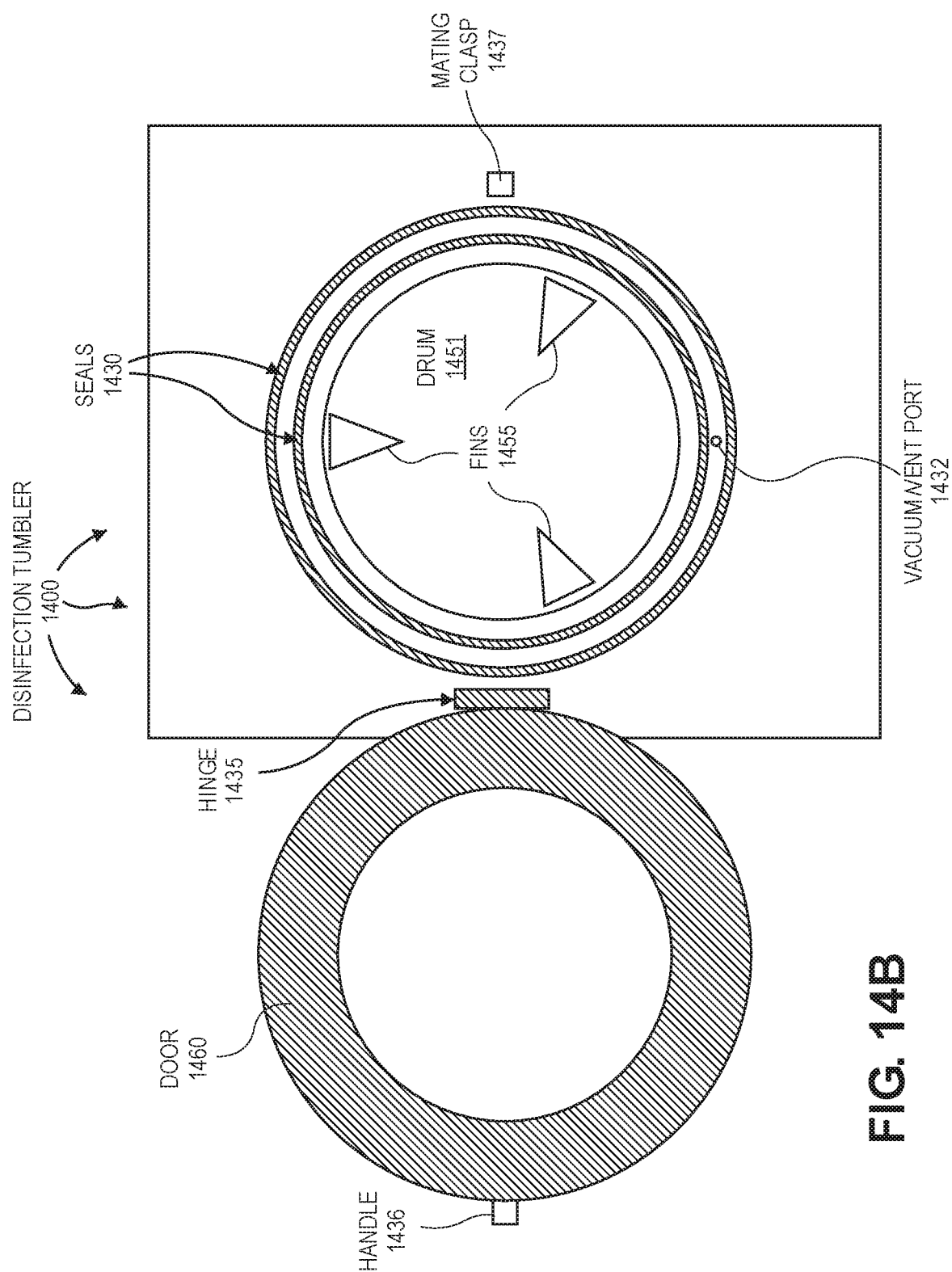
FIG. 14B illustrates an example disinfection tumbler in an open configuration.

FIG. 14B illustrates disinfection tumbler 1400 in an open configuration. As depicted, disinfection tumbler 1400 includes a pair expanding (inflatable) seals 1430 to prevent ozone from escaping drum 1451. The front panel of door 1460 is configured to allow inflatable, expanding seals 1430 close and direct contact between other parts of door 1460 and disinfection tumbler 1400 when seals 1430 are inflated.

The controller can inflate seals 1430 prior to articles inside disinfection tumbler 1400 being disinfected and can maintain inflation during disinfection (e.g., during a disinfection/sterilization cycle). When inflated, seals 1430 prevent atmosphere (and thus ozone) inside disinfection tumbler 1400 from escaping outside of disinfection tumbler 1400. Seals 1430 can remain deflated when disinfection tumbler 1400 is not being used for disinfecting. When deflated, seals 1330 retract and do not contact with other components of door 1406. As such, wear on seals 1430 is reduced when door 1460 is opened and closed. Similar inflatable, expanding seals can be used on any other doors and/or drawers of disinfection tumbler 1400 to prevent atmosphere (and thus ozone) from escaping outside of disinfection tumbler 1400.

Additionally, (articulated) hinge 135 allows close and direct contact between door 1460 and the sealing surface and latching handle 1436 that locks into mating clasp 1437. Locking door 1460 into mating clasp 1437, prevents door 1460 from opening during a disinfection/sterilization cycle. Vacuum/Vent port 1432 can be used to evacuate atmosphere from the gap between seals 1430 (e.g., during a preparation cycle) and vent atmosphere into the gap between seals 1430 (e.g., during an open cycle).

The gap between vacuum seals 1430 can be monitored to verify seal integrity. A detected increase in pressure between the seals 1430 indicates that the seal has been compromised. If ozone is detected between seals 1430, disinfection tumbler 1400 can perform a shutdown, including transitioning to a reduction cycle (possibly prior to complete disinfection).

Thus generally, an ozone generator can be contained internally in a confined volume (e.g., in container 100, in supply cart 1000, in garment disinfection cabinet 1300, in disinfection tumbler 1440, etc.). The confined volume can be sealed to isolate the atmosphere inside the confined volume from an external atmosphere. Double expanding seals can be used to seal doors, drawers, etc. preventing ozone from exiting the sealed, confined volume. Atmosphere between the seals can be evacuated (vacuumed) and monitoring for leaks. The ozone generator can generate ozone from Oxygen ($O_2$) contained within the sealed, confined volume. The sealed, confined volume isolates ozone exposure volume and maintains ozone concentrations below 20 ppb outside of the sealed, confined volume.

Aspects include repeatedly processing the atmosphere inside a sealed, confined volume to generate high concentrations of ozone (e.g., of up to 0.5% atomic) in the sealed, confined volume for disinfection and/or sterilization of medical articles. In one aspect, an ozone concentration of 0.5% atomic is achieved in approximately five minutes. Ozone can be created from Oxygen ($O_2$) using one or more of: corona discharge or ultra-violet light. Oxygen ($O_2$) for ozone generation can include one more of: atmospheric air, bottled Oxygen ($O_2$) (e.g., up to 99.999% purity), elevated Oxygen ($O_2$) concentrated air from an onboard oxygen concentrator. As such, using an oxygen concentrator to increase the partial pressure of Oxygen ($O_2$) in a sealed, confined volume or purging a sealed, confined volume with (e.g., hospital grade) Oxygen ($O_2$) can facilitate generation of high concentrations of ozone.

Aspects also include high-rate reduction of ozone, for example, reducing ozone concentrations from 0.5% to <50 ppb (atomic) in under 60 seconds. An ozone reduction chamber can include a hollow vertical tube (cylindrical or rectangular in cross section open on both ends containing a catalyst of Manganese Dioxide ("$MnO_2$")) (or other suitable catalyst). Manganese Dioxide can be used in an in situ, ozone reduction column. Atmosphere in a sealed, confined volume can be passed through the ozone reduction chamber multiple times to reduce the volume of catalyst for reducing ozone.

Aspects of rapid generation of high concentrations of ozone and rapid reduction to safe levels of ozone can be scaled to almost any size and dimension.

Ozone concentrations can be measured by monitoring the absorption of modulated ultraviolet (UV) light from a light emitting diode (LED) using a broadband light detector. In one aspect, the LED is configured to emit UV light at a wavelength between 240 nm-260 nm (i.e., 250 nm, +/−10 nm) and the light detector is configured to detect the light emitted at the wavelength. In another aspect, the LED is configured to emit UV light at a wavelength between 250 nm-260 nm (i.e., 255 nm, +/−5 nm) and the light detector is configured to detect the light emitted at the wavelength. The LED can be modulated for better signal extraction from noise. Ambient UV light can be blocked from entering the sealed, confined volume using materials opaque to UV light (some materials that are transparent to visible light are opaque to UV light, such as, many poly-carbonate mixtures).

UV light can be monitored to determine when ozone concentration in a sealed, confined volume has achieved a threshold level for disinfection/sterilization. UV light can be monitored to determine a level of contamination in a sealed, confined volume. UV light can be monitored determine when disinfection/sterilization of a medical article in a sealed, confined volume a is complete. UV light can be monitored to determine when ozone concentration in a sealed, confined volume is sufficiently low and/or below a threshold indicating is safe to open a door, drawer, etc. into the confined volume. UV light remains inside the sealed, confined volume protecting operators from UV exposure.

Components in a sealed, confined volume can be constructed of materials that are compatible with ozone exposure. That is, materials that do not break down when exposed to ozone.

In some aspects, controller 131, information screen 202, and communication ports 203 (as well as similar components at any of supply cart 1000, garment disinfection cabinet 1300, or disinfection tumbler 1400) are part of a computing device. Thus, controller 131 (or a controller at any of supply cart 1000, garment disinfection cabinet 1300, or disinfection tumbler 1400) may be a special-purpose processor or general-purpose processor.

Figure 15:
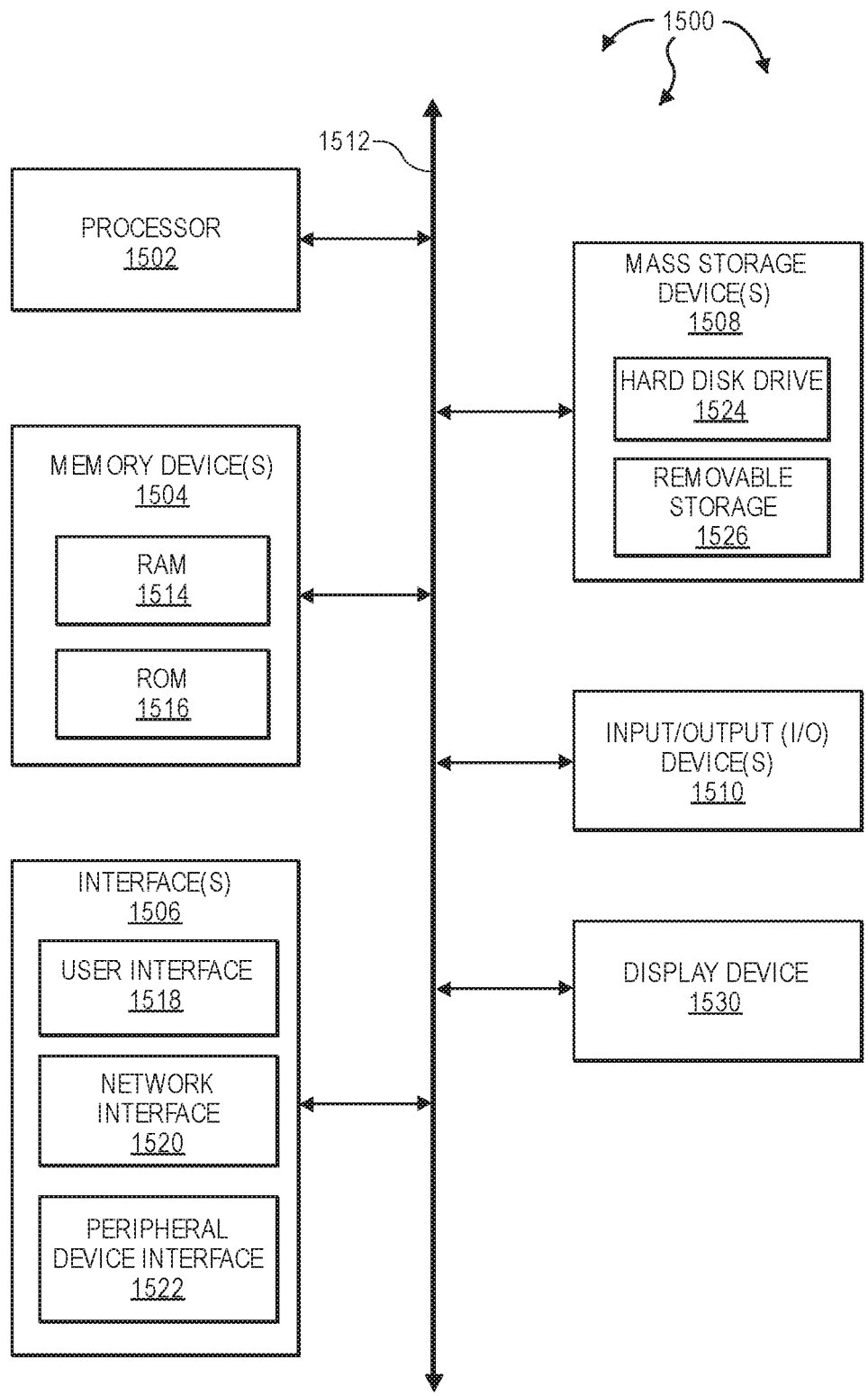
FIG. 15 illustrates an example block diagram of a computing device.

FIG. 15 illustrates an example block diagram of a computing device 1500. Computing device 1500 can be used to perform various procedures, such as those discussed herein. Computing device 1500 can function as a server, a client, or any other computing entity. Computing device 1500 can perform various communication and data transfer functions as described herein and can execute one or more application programs, such as the application programs described herein. Computing device 1500 can be any of a wide variety of computing devices, such as a mobile telephone or other mobile device, a desktop computer, a notebook computer, a server computer, a handheld computer, tablet computer and the like.

Computing device 1500 includes one or more processor(s) 1502, one or more memory device(s) 1504, one or more interface(s) 1506, one or more mass storage device(s) 1508, one or more Input/Output (I/O) device(s) 1510, and a display device 1530 all of which are coupled to a bus 1512. Processor(s) 1502 include one or more processors or controllers that execute instructions stored in memory device(s) 1504 and/or mass storage device(s) 1508. Processor(s) 1502 may also include various types of computer storage media, such as cache memory.

Memory device(s) 1504 include various computer storage media, such as volatile memory (e.g., random access memory (RAM) 1514) and/or nonvolatile memory (e.g., read-only memory (ROM) 1516). Memory device(s) 104 may also include rewritable ROM, such as Flash memory.

Mass storage device(s) 1508 include various computer storage media, such as magnetic tapes, magnetic disks, optical disks, solid state memory (e.g., Flash memory), and so forth. As depicted in FIG. 15, a particular mass storage device is a hard disk drive 1524. Various drives may also be included in mass storage device(s) 1508 to enable reading from and/or writing to the various computer readable media. Mass storage device(s) 108 include removable media 1526 and/or non-removable media.

I/O device(s) 1510 include various devices that allow data and/or other information to be input to or retrieved from computing device 1500. Example I/O device(s) 1510 include cursor control devices, keyboards, keypads, barcode scanners, microphones, monitors or other display devices, speakers, printers, network interface cards, modems, cameras, lenses, radars, CCDs or other image capture devices, and the like.

Display device 1530 includes any type of device capable of displaying information to one or more users of computing device 1500. Examples of display device 1530 include a monitor, display terminal, video projection device, and the like.

Interface(s) 1506 include various interfaces that allow computing device 1500 to interact with other systems, devices, or computing environments as well as humans. Example interface(s) 106 can include any number of different network interfaces 120, such as interfaces to personal area networks (PANs), local area networks (LANs), wide area networks (WANs), wireless networks (e.g., near field communication (NFC), Bluetooth, Wi-Fi, etc., networks), and the Internet. Other interfaces include user interface 1518 and peripheral device interface 1522.

Bus 1512 allows processor(s) 1502, memory device(s) 1504, interface(s) 1506, mass storage device(s) 1508, and I/O device(s) 1510 to communicate with one another, as well as other devices or components coupled to bus 1512. Bus 1512 represents one or more of several types of bus structures, such as a system bus, PCI bus, IEEE 1394 bus, USB bus, and so forth.

In one aspect, one or more processors are configured to execute instructions (e.g., computer-readable instructions, computer-executable instructions, etc.) to perform any of a plurality of described operations. The one or more processors can access information from system memory and/or store information in system memory. The one or more processors can transform information between different formats.

System memory can be coupled to the one or more processors and can store instructions (e.g., computer-readable instructions, computer-executable instructions, etc.) executed by the one or more processors. The system memory can also be configured to store any of a plurality of other types of data generated by the described components.

Accordingly, implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash or other vehicle computer, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors, and may include hardware logic/electrical circuitry controlled by the computer code. These example devices are provided herein purposes of illustration, and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications, variations, and combinations are possible in light of the above teaching. Further, it should be noted that any or all of the aforementioned alternate implementations may be used in any combination desired to form additional hybrid implementations of the disclosure.

What is claimed:

1. A container comprising:
   a disinfection chamber;
   an ozone generation chamber;
   an ozone reduction chamber;
   one or more ozone sensors configured to monitor a concentration of ozone in the disinfection chamber;
   a first intake port between the ozone generation chamber and the disinfection chamber;
   a first exhaust port between the ozone generation chamber and the disinfection chamber;
   a second intake port between the ozone reduction chamber and the disinfection chamber;
   a second exhaust port between the ozone reduction chamber and the disinfection chamber;
   a door openable into an open configuration to permit access to the disinfection chamber and closable into a closed configuration to prevent access to the disinfection chamber;
   a pair of inflatable seals including a first seal and a second seal, the pair of inflatable seals configured to seal against the door when inflated and when the door is in the closed configuration preventing atmosphere in the disinfection chamber from exiting the container;
   a gap between the first seal and the second seal; and
   a vacuum/vent port in the gap.

2. The container of claim 1, wherein the ozone generation chamber further comprises:
   an ozone generator configured to generate ozone into the atmosphere of the ozone generation chamber; and
   a fan configured to recirculate atmosphere from the disinfection chamber through the first intake port into the ozone generation chamber and from the ozone generation chamber through the first exhaust port back into the disinfection chamber.

3. The container of claim 1, wherein the ozone reduction chamber further comprises:
   a catalyst configured to reduce the ozone concentration in atmosphere passing through the catalyst; and
   a fan configured to recirculate atmosphere from the disinfection chamber through the second intake port into the catalyst and from the catalyst through the second exhaust port back into the disinfection chamber.

4. The container of claim 1, further comprising:
   a carriage configured to move inside the container; and
   a hanger attached to the carriage.

5. The container of claim 1, further comprising:
   a rotating drum;
   a plurality of fins attached to the inside of the rotating drum.

6. The container of claim 1, further comprising a plurality of indicator lights on an external surface of the container, the plurality of indicator lights configured to indicate a disinfection status of articles inside the container.

7. A container comprising:
   a disinfection chamber;
   an ozone generation chamber;
   an ozone reduction chamber;
   one or more ozone sensors configured to monitor a concentration of ozone in the disinfection chamber;
   a first intake port between the ozone generation chamber and the disinfection chamber;
   a first exhaust port between the ozone generation chamber and the disinfection chamber;
   a second intake port between the ozone reduction chamber and the disinfection chamber;
   a second exhaust port between the ozone reduction chamber and the disinfection chamber;
   a drawer openable into an open configuration to permit access to the disinfection chamber and closable into a closed configuration to prevent access to the disinfection chamber;
   a pair of inflatable seals including a first seal and a second seal, the pair of inflatable seals configured to seal against the drawer when inflated and when the drawer is in the closed configuration preventing atmosphere in the disinfection chamber from exiting the container;

a gap between the first seal and the second seal; and
a vacuum/vent port in the gap.

8. The container of claim 7, wherein the ozone generation chamber further comprises:
an ozone generator configured to generate ozone into the atmosphere of the ozone generation chamber; and
a fan configured to recirculate atmosphere from the disinfection chamber through the first intake port into the ozone generation chamber and from the ozone generation chamber through the first exhaust port back into the disinfection chamber.

9. The container of claim 7, wherein the ozone reduction chamber further comprises:
a catalyst configured to reduce the ozone concentration in atmosphere passing through the catalyst; and
a fan configured to recirculate atmosphere from the disinfection chamber through the second intake port into the catalyst and from the catalyst through the second exhaust port back into the disinfection chamber.

10. The container of claim 7, further comprising:
a carriage configured to move inside the container; and
a hanger attached to the carriage.

11. The container of claim 1, further comprising a plurality of indicator lights on an external surface of the container, the plurality of indicator lights configured to indicate a disinfection status of articles inside the container.

12. The container of claim 7, wherein the drawer comprises a perforated bottom.

13. The container of claim 12, further comprising:
one or more rollers;
component that causes articles in the drawer to change positions as the one or more rollers roll; and
wherein the one or more rollers are arranged between the perforated bottom and the component.

14. A disinfection system comprising:
a disinfection chamber including one or more ozone sensors configured to monitor a concentration of ozone in the disinfection chamber;
a first intake port between an ozone generation chamber and the disinfection chamber;
a first exhaust port between the ozone generation chamber and the disinfection chamber;
a second intake port between an ozone reduction chamber and the disinfection chamber; and
a second exhaust port between the ozone reduction chamber and the disinfection chamber;
the ozone generation chamber including:
an ozone generator configured to generate ozone into the atmosphere of the ozone generation chamber; and
a first fan configured to recirculate atmosphere from the disinfection chamber through the first intake port into the ozone generation chamber and from the ozone generation chamber through the first exhaust port back into the disinfection chamber;
the ozone reduction chamber including:
a catalyst configured to reduce the ozone concentration in atmosphere passing through the catalyst; and
a second fan configured to recirculate atmosphere from the disinfection chamber through the second intake port into the catalyst and from the catalyst through the second exhaust port back into the disinfection chamber;
a controller; and
system memory coupled to the controller and storing instructions configured to cause the controller to:
close the second intake port and the second exhaust port;
open the first intake port and the first exhaust port;
activate the ozone generator and the first fan;
detect ozone concentration in the disinfection chamber above a threshold ozone concentration;
subsequent to detecting ozone concentration above the threshold ozone concentration, control the ozone concentration in the disinfection chamber to disinfect an article inside the disinfection chamber;
subsequent to disinfection:
deactivate the ozone generator and the first fan;
close the first intake port and the first exhaust port;
open the second intake port and the second exhaust port;
activate the second fan; and
detect ozone concentration in the disinfection chamber below a safe threshold ozone concentration.

15. The disinfection system of claim 14, further comprising a plurality of indicator lights.

16. The disinfection system of claim 15, further comprising the system memory storing instructions configured to cause the controller to activate one of the plurality of indicator lights to indicate that the disinfection system is "in use" subsequent to activating the ozone generator and prior to monitoring ozone concentration below the safe threshold ozone concentration.

17. The disinfection system of claim 15, further comprising the system memory storing instructions configured to cause the controller to activate one of the plurality of indicator lights to indicate that the disinfection system has completed disinfecting the article subsequent to monitoring ozone concentration below the safe threshold ozone concentration.

18. The disinfection system of claim 14, further comprising:
a door openable to permit access to inside the disinfection chamber and closeable to prevent access to inside the disinfection chamber;
a pair of inflatable seals including a first seal and a second seal;
a vacuum/vent port in a gap between the first seal and the second seal; and
further comprising the system memory storing instructions configured to cause the controller to, prior to activating the ozone generator:
detect that the door is closed;
lock the door;
inflate the first seal and inflate the second seal;
evacuate atmosphere in the gap through the vacuum/vent port; and
monitor the gap for pressure changes.

19. The disinfection system of claim 18, further comprising the system memory storing instructions configured to cause the controller to, subsequent to detecting ozone concentration below the safe threshold ozone concentration:
vent atmosphere into the gap through the vacuum/vent port;
deflate the first seal and deflate the second seal; and
unlock the door.

20. The disinfection system of claim 14, wherein the disinfection chamber includes a removable supply board comprising one or more clips configured to hold medical articles and one or more hooks configured to hold medical articles.

* * * * *